(12) United States Patent
Yang et al.

(10) Patent No.: US 11,840,582 B2
(45) Date of Patent: Dec. 12, 2023

(54) SYNTHESIS METHOD OF CYCLOSPORINE DERIVATIVES

(71) Applicant: Peking University Shenzhen Graduate School, Shenzhen (CN)

(72) Inventors: Zhen Yang, Shenzhen (CN); Qingzhou Zhang, Shenzhen (CN); Fengxia Li, Shenzhen (CN); Chongguo Jiang, Shenzhen (CN); Jianxian Gong, Shenzhen (CN); Jun Huang, Shenzhen (CN); Weibin Zhang, Shenzhen (CN)

(73) Assignee: Peking University Shenzhen Graduate School, Shenzhen (CN)

( * ) Notice: Subject to any disclaimer, the term of this patent is extended or adjusted under 35 U.S.C. 154(b) by 222 days.

(21) Appl. No.: 17/373,369

(22) Filed: Jul. 12, 2021

(65) Prior Publication Data
US 2022/0315626 A1  Oct. 6, 2022

(30) Foreign Application Priority Data
Mar. 18, 2021  (CN) .......................... 202110291235.0

(51) Int. Cl.
*C07K 7/64* (2006.01)
*B01D 11/04* (2006.01)
(Continued)

(52) U.S. Cl.
CPC .......... *C07K 7/645* (2013.01); *B01D 11/0492* (2013.01); *B01D 15/426* (2013.01);
(Continued)

(58) Field of Classification Search
CPC ....... C07K 1/1077; C07K 1/113; C07K 7/645
See application file for complete search history.

(56) References Cited

U.S. PATENT DOCUMENTS 9,200,038 B2   12/2015  Hegmans et al.
9,493,511 B2   11/2016  Frydrych et al.
(Continued)

FOREIGN PATENT DOCUMENTS

| CN | 103328497 A | 9/2013 |
| CN | 103443119 A | 12/2013 |
| CN | 109476705 A | 3/2019 |
| WO | 2016160362 A1 | 10/2016 |
| WO | 2022193482 A1 | 9/2022 |

OTHER PUBLICATIONS

Li et al. Semisynthesis of CRV431. Organic Letters. Apr. 12, 2021, vol. 23, pp. 3421-3425. (Year: 2021).*
(Continued)

*Primary Examiner* — Jeffrey E. Russel
(74) *Attorney, Agent, or Firm* — Kagan Binder, PLLC

(57) ABSTRACT

The present disclosure relates to a method of synthesizing cyclosporine derivatives. The method includes: providing a precursor fluid of the cyclosporine derivative, an alkaline fluid and a $ClCH_2OCOCl$ solution; premixing the precursor fluid and the alkaline fluid to obtain a premixed solution; feeding the premixed solution into a first reaction chamber, reacting to prepare a first reaction liquid; feeding the first reaction liquid into a second reaction chamber, reacting the first reaction liquid with a $CO_2$ fluid to prepare a second reaction liquid; and reacting the second reaction liquid with the $ClCH_2OCOCl$ solution.

17 Claims, 4 Drawing Sheets

(51) Int. Cl.
  *B01D 15/42*   (2006.01)
  *C07K 1/107*   (2006.01)
  *C07K 1/14*    (2006.01)
  *C07K 1/16*    (2006.01)
  *G01N 30/14*   (2006.01)
  *G01N 30/02*   (2006.01)

(52) U.S. Cl.
  CPC ............ *C07K 1/1077* (2013.01); *C07K 1/145* (2013.01); *C07K 1/16* (2013.01); *G01N 30/14* (2013.01); *G01N 2030/027* (2013.01)

(56) References Cited

U.S. PATENT DOCUMENTS

2016/0289271 A1* 10/2016 Pettit ................. C07K 7/645
2022/0331397 A1  10/2022 Su et al.

OTHER PUBLICATIONS

International Seach Report, and English translation thereof, for International Application No. PCT/CN2021/104692, dated Dec. 24, 2021, (13 pages).

Li et al., "Semi-Synthesis of CRV431," Organic Letters, vol. 23, No. 9, pp. 3421-3425, Apr. 12, 2021, (147 pages).

Wang et al., "Development of flow chemistry in pharmaceutical synthesis," Central South Pharmacy, vol. 17, No. 8, pp. 1179-1187, Aug. 31, 2019 (10 pages). (English Abstract only; See International Search Report for PCT/CN2021/104692).

Bogdan et al., "Emerging Trends in Flow Chemistry and Applications to the Pharmaceutical Industry," Journal of Medicinal Chemistry, vol. 62, No. 14, pp. 6422-6468, Feb. 22, 2019, (47 pages).

Chinese Office Action for Chinese Counterpart Application No. 202110291235.0, dated May 20, 2023, (6 pages).

* cited by examiner

SYNTHESIS METHOD OF CYCLOSPORINE DERIVATIVES

CROSS-REFERENCE TO RELATED APPLICATION

This application claims the benefit of priority of Chinese Patent Application No. 202110291235.0, filed 18 Mar. 2021, the content of which is incorporated by reference in its entirety for all purposes.

TECHNICAL FIELD

The present disclosure relates to a technical field of chemical synthesis, in particular to a method of synthesizing cyclosporine derivatives.

BACKGROUND

Cyclosporine A (CsA) is a natural product of cyclic undecapeptides containing 7 N-methyl, which is isolated from the metabolites of soil fungi and has a immunosuppressive activity. In 1983, CsA was first used as an immunosuppressive drug for the treatment of immune rejection after kidney transplantation, which significantly improved the survival rate of patients after organ transplantation. The emergence of CsA is a revolution in the field of organ transplantation. Due to its immunosuppressive and anti-inflammatory activities, CsA is also used to treat diseases such as immune-related diseases, inflammation or metabolic diseases. However, the immunosuppressive activity of CsA can produce toxic and side effects when it treats inflammation, infection and metabolic diseases. Therefore, modifying the structure of CsA, removing its immunosuppressive activity, while retaining or improving its anti-inflammatory and anti-infective activities, is the current research focus of CsA.

In the structural modification of CsA, [methylene-sar]$^3$CsA is an important intermediate, which can undergo Michael addition reaction with thiol compounds under alkaline conditions to synthesize a series of CsA derivatives with antiviral activity. In addition, [methylene-sar]$^3$CsA can also be used in the synthesis of [D-MeAla]$^3$CsA and derivatives thereof. Therefore, the synthesis of [methylene-sar]$^3$CsA has very important value. However, the traditional method of synthesizing [methylene-sar]$^3$CsA is relatively backward and needs to be improved urgently.

The synthesis of [methylene-sar]$^3$CsA was first reported by Allergan Company in 2012. The synthesis route is as follows:

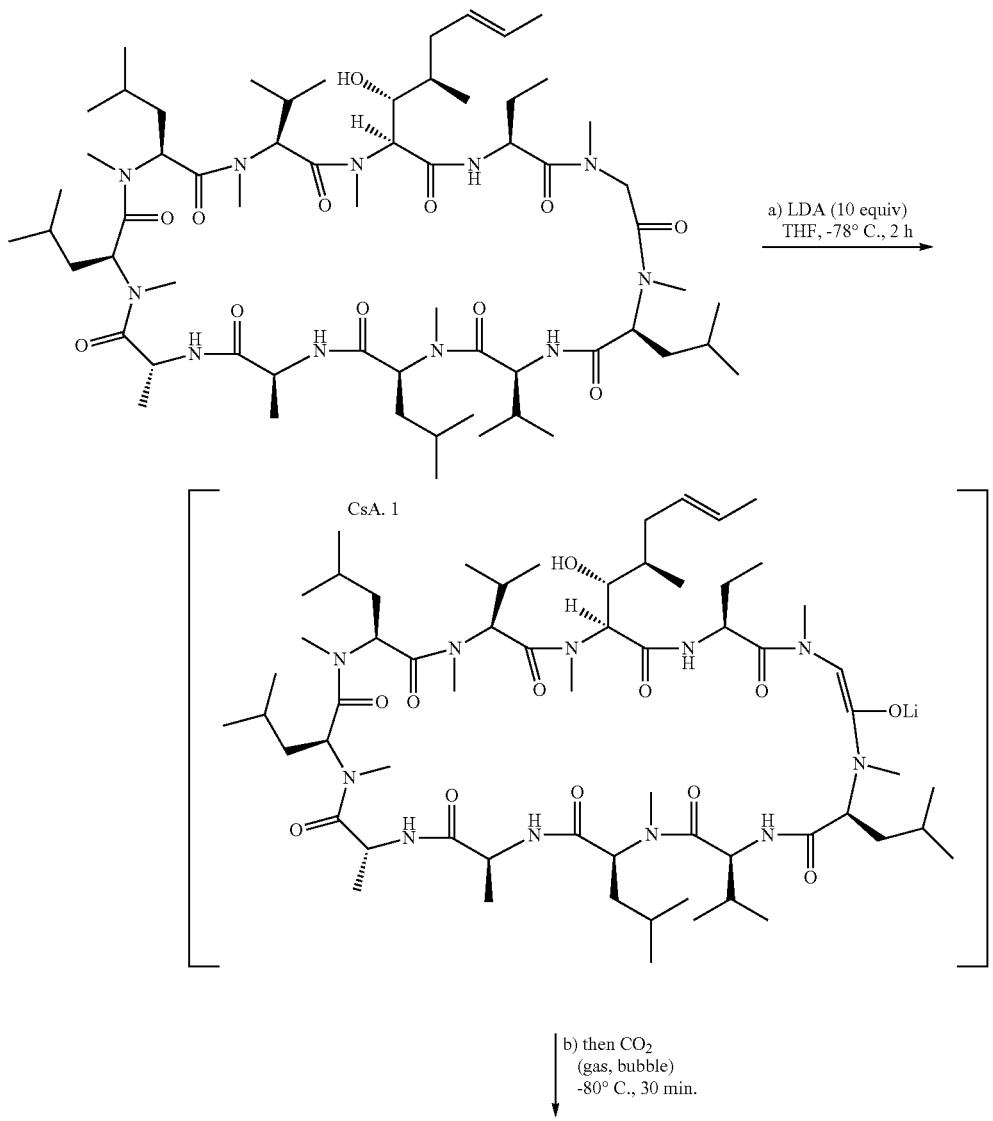

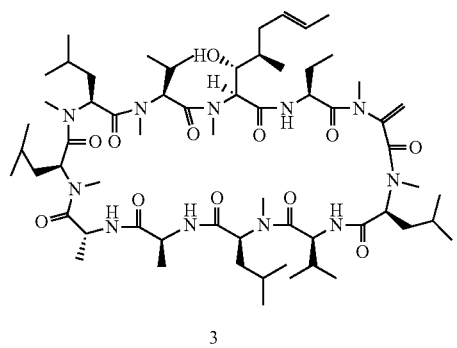

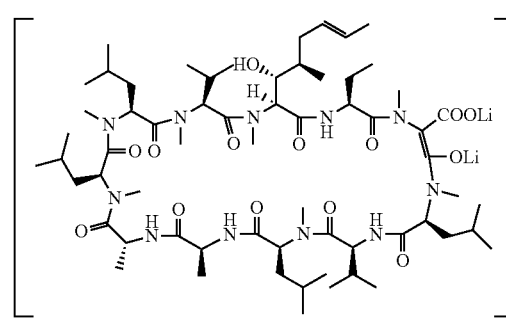

c) -50° C. to 15° C.
then -50° C.
ClCO₂CH₂Cl, 8 h d) H⁺

-40% yield dissolving 1 (CsA) in dry THF solvent, adding lithium diisopropylamide (LDA) (10 equiv.) dropwise at −78° C., while preventing moisture, and reacting for 2 h. Then reducing the temperature to −50° C., and introducing dry $CO_2$ gas slowly into the reaction solution for about 30 minutes, and then reacting for 3 h. The temperature can be slowly raised to room temperature. Then reducing the temperature to −50° C., adding ClCOOCH₂Cl (10 equiv.), and reacting overnight, then subjecting to post-treatment, and purifying to obtain [methylene-sar]³CsA 3.

The synthetic route can be completed in one step, and the yield is basically about 40%. However, in practical applications, this method has complicated operations, high risk, and poor reproducibility, which limits the large-scale preparation of [methylene-sar]³CsA. This is manifested in: First, there is a need to add excessive LDA during the reaction process, the risk is high; Second: there are multiple extremely low temperature adjustments, such as when adding LDA, the temperature of the reaction solution needs to be reduced to −78° C. and reacted for 2 hours, the temperature is slowly raised to room temperature, and then the temperature is lowered to −50° C., thus the operation was cumbersome; Third: the process of bubbling and releasing of dry carbon dioxide at −50° C. would also complicate the reaction process.

SUMMARY

Accordingly, the present disclosure provides a method of synthesizing a cyclosporine derivative. In one aspect of the present disclosure, there a method of synthesizing a cyclosporine derivative is provided, which is represented by the following Formula (I):

Formula (I)

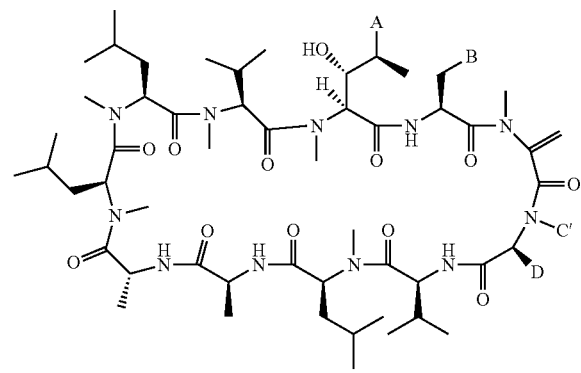

wherein A is at least one selected from the group consisting of —CH═CHR, —CH═CH—CH═CHR and —CH₂CH₂R; R is at least one selected from the group consisting of —CH₃, —CH₂SH, —CH₂S—R₁, —CH₂—COOR₁', —COOR₁', —R₂—COOR₁', and CH₂—R₂—COOR₁'; R₁ is C1~C6 alkyl; R₂ is C1~C6 alkoxy, R₁' is H, ammonium salt or C1~C6 alkyl;

B is at least one selected from the group consisting of —CH₃, —CH₂CH₃, —CH(OH)CH₃, —CH(CH₃)₂, and —CH₂CH₂CH₃;

C' is at least one selected from the group consisting of —H, —CH₃, —CH₂CH₃, and —CH₂CH₂CH₃; and D is at least one selected from the group consisting of —CH₂CH(CH₃)₂, —CH₂C(OH)(CH₃)₂, —CH(CH₃)CH₂CH₃ and —CH₂CH₂-[4-(2-CH₃OCH₂CH₂)-1-R₃];

R₃ is piperazinyl;

the method includes:

providing a precursor fluid, an alkaline fluid, and a ClCH₂OCOCl solution; wherein a precursor in the precursor fluid is represented by Formula (II):

Formula (II)

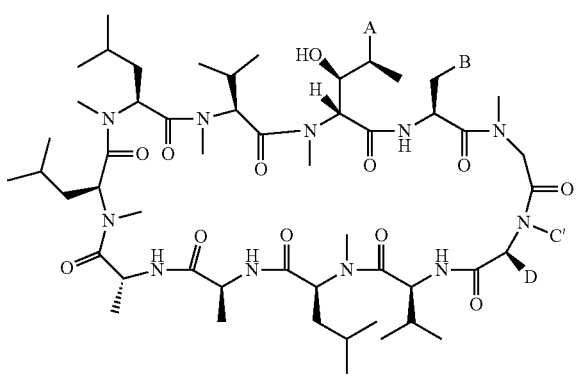

premixing the precursor fluid and the alkaline fluid to obtain a premixed solution;

feeding the premixed solution into a first reaction chamber, reacting to prepare a first reaction liquid;

feeding the first reaction liquid into a second reaction chamber, reacting the first reaction liquid with a $CO_2$ fluid to prepare a second reaction liquid; and reacting the second reaction liquid with the ClCH₂OCOCl solution.

In one embodiment, the precursor fluid is fed with a flow rate of 0.03 mM/min to 0.06 mM/min; feeding the alkaline fluid has a flow rate of 0.1 mM/min to 0.5 mM/min, and the molar flow rate ratio of CsA to alkali liquor is 8 to 20.

In one embodiment, the precursor fluid and the alkaline fluid are fed into the first reaction chamber at a temperature of −5° C. to 30° C., and with a time of 50 s to 90 s.

In one embodiment, the $CO_2$ fluid has a flow rate of 5 mL/min to 12 mL/min.

In one embodiment, the first reaction liquid is fed into the second reaction chamber to react with the $CO_2$ fluid at a temperature of −20° C. to 30° C., and with a time of 3 s to 20 s.

In one embodiment, the molar concentration of $ClCH_2OCOCl$ solution is 0.3 M to 0.7 M.

In one embodiment, the molar concentration of the precursor in the precursor fluid is 0.01 M to 0.055 M.

In one embodiment, the molar concentration of alkali in the alkaline fluid is 0.1 M to 0.3 M.

In one embodiment, the molar ratio of the precursor, alkali and $CO_2$ is 1:(8~15):(8~25).

In one embodiment, reacting the second reaction solution with the $ClCH_2OCOCl$ solution includes: collecting the second reaction solution into the $ClCH_2OCOCl$ solution at a temperature of −55° C. to −45° C. to prepare a third reaction solution; and warming the third reaction solution to room temperature naturally and reacting for 3 h to 20 h.

In one embodiment, the solvents of the precursor fluid, the alkaline fluid, and the $ClCH_2OCOCl$ solution are at least one selected from the group consisting of 2-methyltetrahydrofuran, tetrahydrofuran, n-hexane, methyl tert-butyl ether, and diethyl ether.

In one embodiment, the method further includes: adding water to the third reaction solution to adjust the pH of the third reaction solution to 7 to 8, concentrating the third reaction solution under reduced pressure, extracting the third reaction solution with ethyl acetate, and collecting the organic phase, and purifying the organic phase by column chromatography.

In one embodiment, the mobile phase used in the column chromatography is dichloromethane and methanol with a volume ratio of (15~25):1.

In one embodiment, the precursor is cyclosporine A; A is —CH═CH—CH$_3$; B is —CH$_3$; C is —CH$_3$; and D is —CH$_2$CH(CH$_3$)$_2$.

In one embodiment, an alkali in the alkaline fluid is at least one selected from the group consisting of lithium diisopropylamide (LDA), lithium bis(trimethylsilyl)amide (LiHMDS), and sodium bis(trimethylsilyl)amide (NaHMDS).

A method of synthesizing a cyclosporine 1,3-position derivative is provided, which includes:

synthesizing a cyclosporine derivative H according to the above-mentioned embodiment;

performing an olefin metathesis action using the cyclosporine derivative H and a compound CH$_2$═CH—R to prepare an intermediate H-1;

performing an asymmetric hydrogenation reaction to the intermediate H-1 to prepare an intermediate H-2; and performing a hydrogenation reaction to the intermediate H-2 to prepare the cyclosporine 1,3-position derivative;

wherein the cyclosporine derivative H is represented by the following Formula (III):

Formula (II)

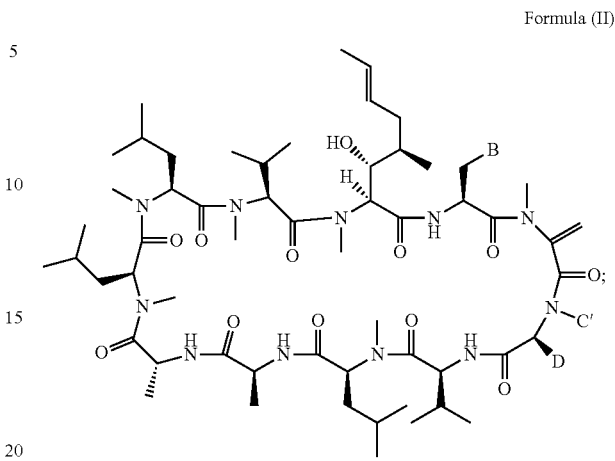

the intermediate H-1 is represented by the following Formula (III-1):

Formula (III-1)

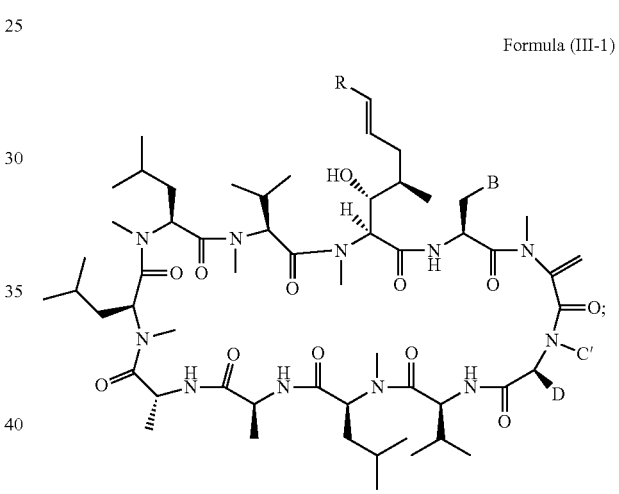

the intermediate H-2 is represented by the following Formula (III-2):

Formula (III-2)

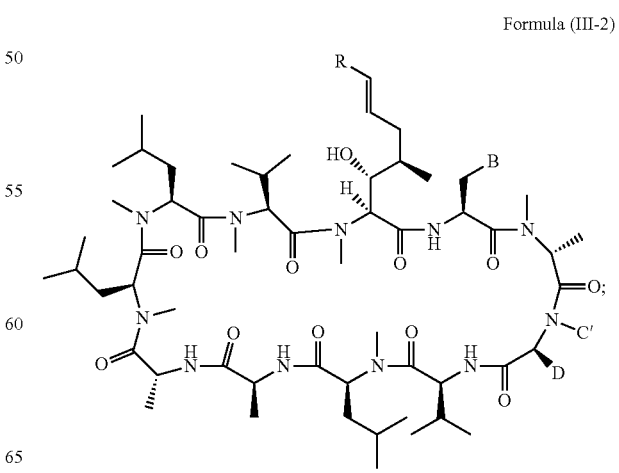

and the cyclosporine 1,3-position derivative is represented by the following Formula (IV):

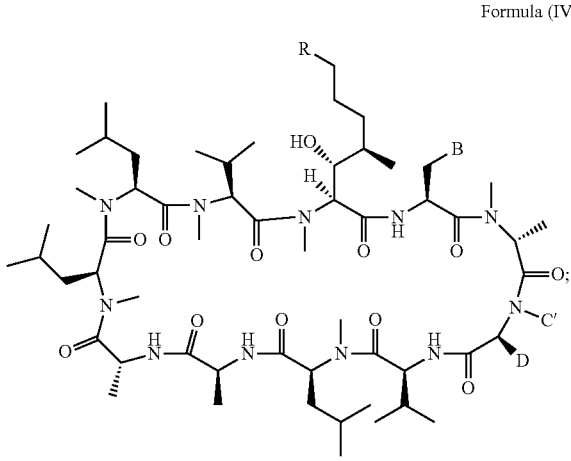

Formula (IV)

wherein R is at least one selected from the group consisting of —$CH_2CH_2CH_2NH(C=O)CH_3$, —$CH_2CH_2CH_2COOH$, and the following groups:

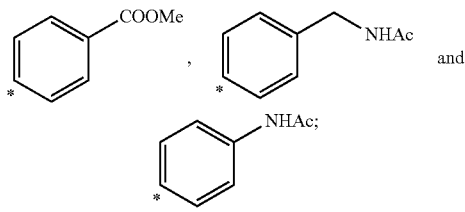

wherein the asterisk indicates the point of attachment.

In one embodiment, the olefin metathesis action comprises a reflux reaction using dichloromethane as a solvent.

The method of synthesizing cyclosporine derivatives of the present disclosure applies flow chemistry technology to the synthesis of cyclosporine derivatives for the first time, and firstly constructs a continuous method of synthesizing cyclosporine derivatives. Compared with the traditional synthesis process, it is greatly optimized the synthesis process of cyclosporine derivatives. The established synthesis process is simple, efficient, easy to post-processing, and the synthesis yield is increased from the traditional 40%, to 65%, which greatly shortens the reaction time, improves the safety, and is simple to operate, easy to prepare on a large scale, and has good reproducibility.

Further, the present disclosure can also achieve the following advantages by adopting suitable reaction parameter settings:

(1) it is greener and atomic economy, and the synthesis safety and yield have been significantly improved;

(2) avoiding a large number of LDA operations, trying to carry out in a low-capacity microreactor, which improves the safety of the process operation;

(3) the side reaction can be avoided under the condition that only one lower temperature (such as 50° C.) adjustment is required, and the synthesis yield is increased. At the same time, during the two-phase reaction between the first reaction solution and $CO_2$, there is also no need to control a lower temperature, so that the overall process operation is simple and easy to scale application.

DETAILED DESCRIPTION OF THE EMBODIMENTS

Figure 1:
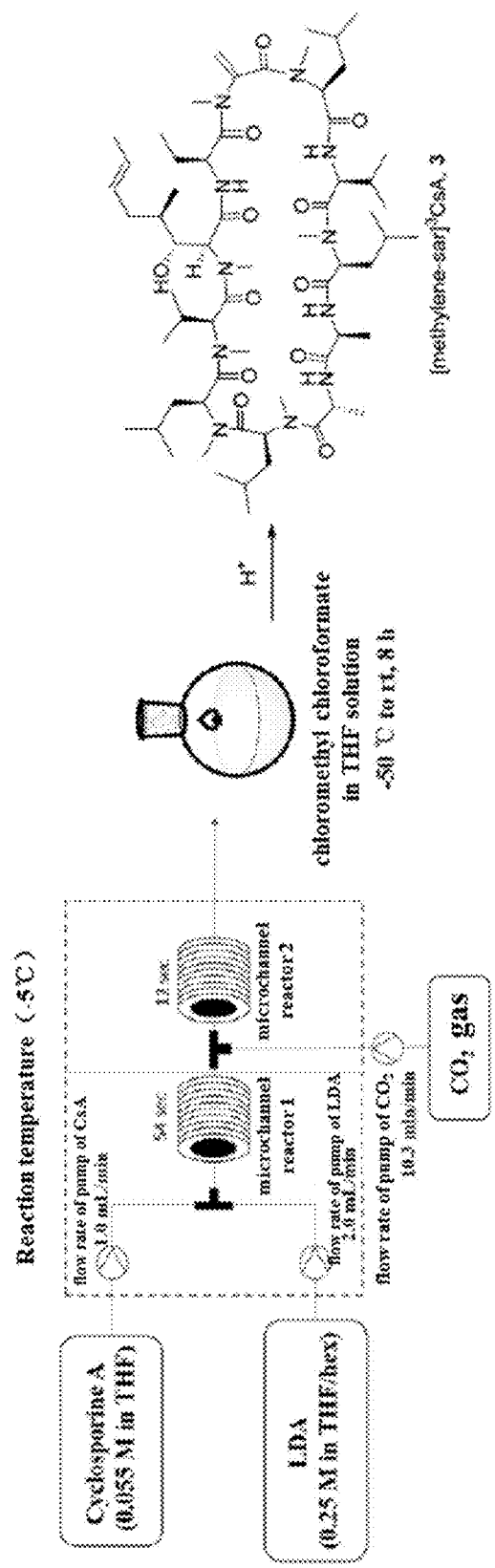
FIG. 1 is a flowchart of a method of synthesizing the cyclosporine derivative [methylene-sar]$^3$CsA 3 according to Example 1.

The method of synthesizing the cyclosporine derivatives of the present disclosure will be further described in detail below with reference to specific examples. The present disclosure may be embodied in many different forms and is not limited to the embodiments described herein. Rather, these embodiments are provided so that the understanding of the disclosure of the present invention will be more thorough and complete.

Unless otherwise defined, all technical and scientific terms used herein have the same meaning as commonly understood by skilled person in the art to which the present disclosure belongs. The terms used in the specification of the present disclosure herein are for the purpose of describing specific embodiments only and are not intended to limit the present disclosure.

The term "alkyl" refers to a saturated hydrocarbon group containing primary (normal) carbon atoms, or secondary carbon atoms, or tertiary carbon atoms, or quaternary carbon atoms, or a combination thereof. Phrases comprising this term, for example, "C1~C6 alkyl" refers to an alkyl containing 1 to 6 carbon atoms, and may independently be C1 alkyl, C2 alkyl, C3 alkyl, C4 alkyl, C5 alkyl, C6 alkyl at each occurrence. Suitable examples include, but are not limited to: methyl (Me, —$CH_3$), ethyl (Et, —$CH_2CH_3$), 1-propyl (normal-propyl, n-Pr, n-propyl, —$CH_2CH_2CH_3$), 2-propyl (i-Pr, i-propyl, —$CH(CH_3)_2$), 1-butyl (normal-butyl, n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), tert-butyl (1,1-dimethyl ethyl, t-Bu, t-butyl, —$C(CH_3)_3$), 1-pentyl (normal-pentyl, n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (normal-hexyl, —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CF_3$), 4-methyl-2-pentyl (—$CH(CH_3)CH_2CH(CH_3)_2$), 3-methyl-3-pentyl (—$ClCH_3)(CH_3CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "alkoxy" refers to a group having an —O-alkyl group, that is, the alkyl as defined above is connected to the core structure via an oxygen atom. Phrases comprising this term, for example, "C1~C6 alkoxy" refers to the alkoxy group containing 1 to 6 carbon atoms, and may independently be C1 alkoxy, C2 alkoxy, 3 alkoxy, C4 alkoxy, C5 alkoxy, C6 alkoxy at each occurrence.

The present disclosure provides a method of synthesizing a cyclosporine derivative represented by the following Formula (I):

Formula (I)

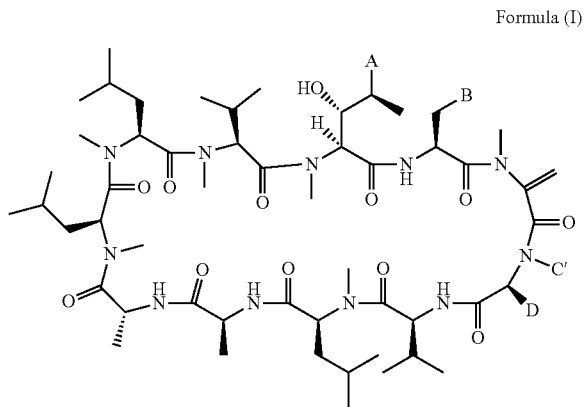

wherein A is at least one selected from the group consisting of —CH=CHR, —CH=CH—CH=CHR, and —CH$_2$CH$_2$R; R is at least one selected from the group consisting of —CH$_3$, —CH$_2$SH, —CH$_2$S—R$_1$, —CH$_2$—COOH, —COOH, —R$_2$—COOH, and CH$_2$—R$_2$—COOH; R$_1$ is C1~C6 alkyl, R$_2$ is C1~C6 alkoxy;

B is at least one selected from the group consisting of —CH$_3$, —CH$_2$CH$_3$, —CH(OH)CH$_3$, —CH(CH$_3$)$_2$, and —CH$_2$CH$_2$CH$_3$;

C' is at least one selected from the group consisting of —H, —CH$_3$, —CH$_2$CH$_3$, and —CH$_2$CH$_2$CH$_3$; and D is at least one selected from the group consisting of —CH$_2$CH(CH$_3$)$_2$, —CH$_2$C(OH)(CH$_3$)$_2$, —CH(CH$_3$)CH$_2$CH$_3$, and —CH$_2$CH$_2$-[4-(2-CH$_3$OCH$_2$CH$_2$)-1-R$_3$];

R$_3$ is piperazinyl.

The method includes.

S1, providing a precursor fluid, an alkaline fluid, and a ClCH$_2$OCOCl solution wherein a precursor in the precursor fluid is represented by Formula (II):

Formula (II)

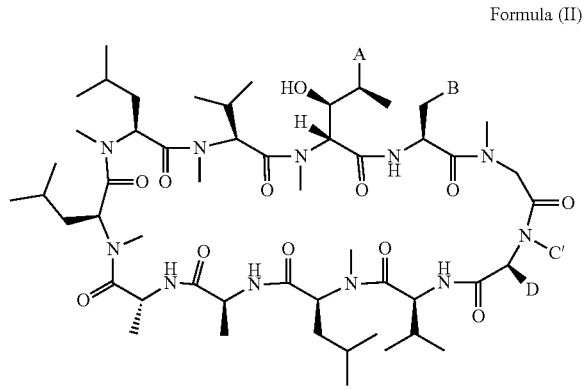

S2, premixing the precursor fluid and the alkaline fluid to obtain a premixed solution;

S3, feeding the premixed solution into a first reaction chamber, reacting to prepare a first reaction liquid;

S4, feeding the first reaction liquid into a second reaction chamber, reacting the first reaction liquid with a CO$_2$ fluid to prepare a second reaction liquid; and S5, reacting the second reaction liquid with the ClCH$_2$OCOCl solution.

The flow chemistry technology is combined with conventional reaction methods (that is, reaction in a reaction flask or reaction still) to prepare cyclosporine derivatives for the first time. The process is simple, the synthesis cycle is short, and the operation is safe, which are beneficial to improve the synthesis yield, and beneficial to realize large-scale production.

In one specific embodiment, the precursor is cyclosporine A (CsA), A is —CH=CH—CH$_3$; B is —CH$_3$; C is —CH$_3$; and D is —CH$_2$CH(CH$_3$)$_2$.

In one specific embodiment, an alkali in the alkaline fluid is at least one selected from the croup consisting of lithium diisopropylamide (LDA), bis(trimethylsilyl)amide (LiHMDS), and sodium bis(trimethylsilyl)amide (NaHMDS).

Step S1 is a preliminary step for reaction, the precursor, alkali and ClCH$_2$OCOCl are respectively prepared in the form of a solution in order to conveniently and continuously carry out the reaction of each step.

In one specific embodiment, the molar concentration of the precursor in the precursor fluid is 0.01 M to 0.055 M.

In one specific embodiment, the molar concentration of alkali in the alkaline fluid is 0.1 M to 0.3 M.

In one specific embodiment, the molar concentration of ClCH$_2$OCOCl solution is 0.3 M to 0.7 M.

In one specific embodiment, the solvents of the precursor fluid, the alkaline fluid and the ClCH$_2$OCOCl solution are at least one selected from the group consisting of 2-methyltetrahydrofuran, tetrahydrofuran, n-hexane, methyl tert-butyl ether, and diethyl ether. Specifically, the solvent used for the precursor fluid is tetrahydrofuran. The solvent used for the alkaline fluid is a mixed solvent of tetrahydrofuran and n-hexane; and the solvent used for the ClCH$_2$OCOCl solution is tetrahydrofuran.

Step S2 is the reaction process of the precursor and the alkali, which is the flow chemical reaction process. By reasonably adjusting the flow rates of the precursor fluid and the alkaline fluid, the raw materials can be fully reacted, with few by-products, high yield, and short reaction time.

In one specific embodiment, the precursor fluid is fed with a flow rate of 0.03 mM/min to 0.06 mM/min; the alkaline fluid is fed with a flow rate of 0.1 mM/min to 0.5 mM/min. In one embodiment of the synthesis method, the flow chemistry technology is used to reduce the amount of alkali, such as lithium diisopropylamide, so as to greatly improve the safety of operation. For example, in some embodiments, the amount of lithium diisopropylamide is only 0.5 mM/min.

In one specific embodiment, the precursor fluid is fed with a flow rate of 1 mL/min to 1.5 mL/min; and the alkaline fluid is fed with a flow rate of 1 mL/min to 3 mL/min. In one embodiment, the molar concentration of the precursor in the precursor fluid is 0.01 M to 0.055 M, and the molar concentration of the alkali in the alkaline fluid is 0.1 M to 0.3 M.

In another embodiment, the precursor fluid is fed with a flow rate of 1 mL/min to 1.5 mL/min; the alkaline fluid is fed with a flow rate of 1.5 mL/min to 2 mL/min.

In one specific embodiment, the molar ratio of the precursor to the alkali is 1:8~20.

In one specific embodiment, the precursor fluid and the alkaline fluid are fed into the first reaction chamber at a temperature of −5° C. to 30° C., and with a time of 50 s to 90 s. In further example, the precursor fluid and the alkaline fluid are fed into the first reaction chamber at a temperature of −5° C. to 0° C., and with a time of is 50 s to 60 s. In one synthesis method of the present disclosure, the reaction process of the precursor and the alkali can be realized at a general low temperature such as −5° C., which avoids the operation at extremely low temperature conditions such as −78° C. in the traditional technology, the operation is simple and easy, and there is no need for extremely low temperature resistant equipment.

Step S4 is the reaction between the first reaction liquid and $CO_2$, which is a flow chemical reaction process, wherein the first reaction liquid is prepared by the reaction of the precursor and the alkali. By reasonably adjusting the flow rate of $CO_2$, the raw materials can be fully reacted, with few by-products, high yield, and short reaction time.

In one specific embodiment, the $CO_2$ fluid is fed with a flow rate of 5 mL/min to 12 mL/min. In another embodiment, the $CO_2$ fluid is fed with a flow rate of 9 mL/min to 11 mL/min.

In one specific embodiment, the molar ratio of the precursor to $CO_2$ is 1:5~20.

In one specific embodiment, the first reaction liquid is fed into the second reaction chamber and $CO_2$ is introduced to perform the reaction at a temperature of −20° C. to 30° C., and with a time of 3 s to 20 s. In another embodiment, the precursor fluid and the alkaline fluid are fed into the first reaction chamber at a temperature of −5° C. to 0° C., and with a time of 10 s to 15 s. In one synthesis method of the present disclosure, the process of reacting with $CO_2$ may be performed at a general low temperature such as −5° C., avoiding the bubbling and releasing process of dry carbon dioxide under the extremely low temperature condition of −50° C. in the traditional technology, and making the operation process simple and easy to carry out, and having low requirements for equipment.

Step S5 is the reaction of the second reaction solution with $ClCH_2OCOCl$.

In one specific embodiment, reacting the second reaction solution with the $ClCH_2OCOCl$ solution includes: collecting the second reaction solution into the $ClCH_2OCOCl$ solution at a temperature of −55° C. to −45° C. to prepare a third reaction solution; and warming the third reaction solution to room temperature naturally and reacting overnight (usually for 3 h to 20 h). In one synthesis method of the present disclosure, the process of reacting the second reaction solution with the $ClCH_2OCOCl$ solution may only keep a lower temperature during the process of adding the second reaction solution, and then it can be naturally warmed to room temperature for reaction, making the operation process simple and easy to carry out, and having low requirements for equipment.

In one specific embodiment, the molar ratio of the precursor, alkali and $CO_2$ during the whole reaction is 1:(8~15):(8~25). In one specific embodiment, the molar ratio of the precursor, alkali and $CO_2$ during the whole reaction is 1:(9~10):(8~13).

Furthermore, the method of synthesizing cyclosporine derivatives also includes a post-treatment step:

In one specific embodiment, the post-treatment includes: adding water to the third reaction solution to adjust the pH of the third reaction solution to 7 to 8; concentrating the third reaction solution under reduced pressure; extracting the third reaction solution with ethyl acetate; and purifying the extract by column chromatography.

In one specific embodiment, the mobile phase used in the column chromatography is dichloromethane and methanol with a volume ratio of (15~25):1.

In one specific embodiment, the temperature of the reactant is cooled to −5° C. to 5° C. before adding water to the reactant.

In one specific embodiment, adjusting the pH of the reactant to 7 to 8 is performed by using an aqueous hydrochloric acid solution.

In one specific embodiment, concentrating under reduced pressure refers to concentrating under reduced pressure to remove the solvent.

CRV431 is an immunosuppressive inhibitor of cyclosporine A for the treatment of non-alcoholic steatohepatitis (NASH) and viral hepatitis developed by the Hepion Company, which is currently in clinical phase II (NCT04480710). CRV431 can effectively inhibit a variety of cyclophilin proteins (CyP), including cyclophilin protein A, cyclophilin protein B, cyclophilin protein H and cyclophilin protein G, with an inhibition constant or $IC_{50}$ between 1 nM and 7 nM, the highest is 13 times that of cyclosporine A inhibiting the activity of cyclophilin protein. So far, CRV431 is the cyclosporine A derivative that inhibits the activity of cyclophilin protein best. Prom the structural point of view, CRV431 is Obtained by multi-step transformation of the side chains on P1 and P3 positions of cyclosporine A, which structure is as follows:

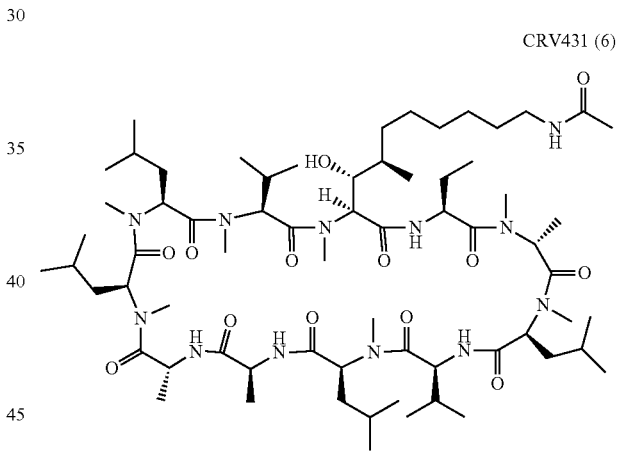

CRV431 (6)

The traditional method for synthesizing CRV431 requires 7 or 8 steps with the total yield of less than 1%. Based on the important biological activity of CRV431 and the backwardness of chemical synthesis methods, there is an urgent need to develop a more concise and effective preparation method for CRV431 and derivatives thereof.

Therefore, the present disclosure also provides a method of synthesizing cyclosporine 1,3-position derivatives, which includes:

synthesizing cyclosporine derivative H according to the above-mentioned method;

performing an olefin metathesis action using the cyclosporine derivative H and a compound $CH_2\!=\!CH\!-\!R$ to prepare an intermediate H-1;

performing an asymmetric hydrogenation reaction to the intermediate H-1 to prepare an intermediate H-2; and performing a hydrogenation reaction to the intermediate H-2 to prepare the cyclosporine 1,3-position derivative;

wherein the cyclosporine derivative H is represented by the following Formula (III):

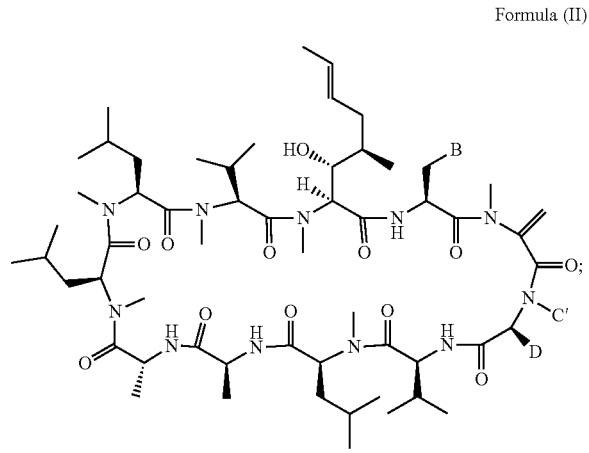

Formula (II)

the intermediate H-1 is represented by the following Formula (III-1):

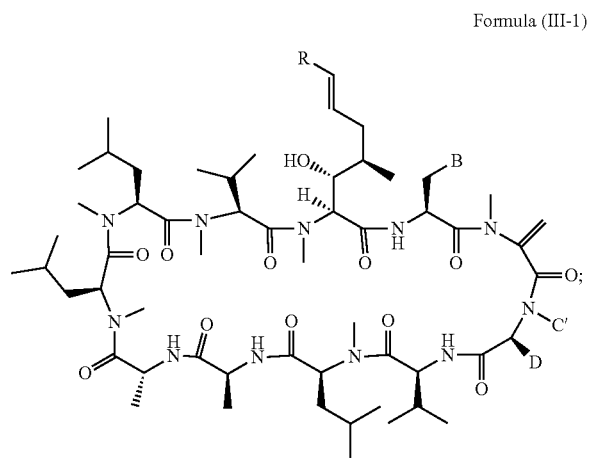

Formula (III-1)

the intermediate H-2 is represented by the following Formula (III-2):

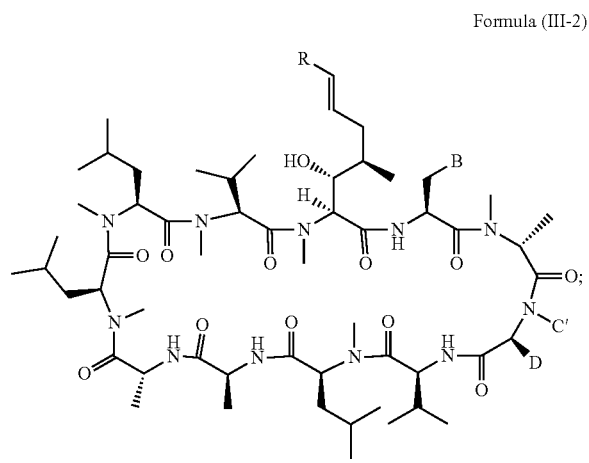

Formula (III-2)

and the cyclosporine 1,3-position derivative is represented by the following Formula (IV):

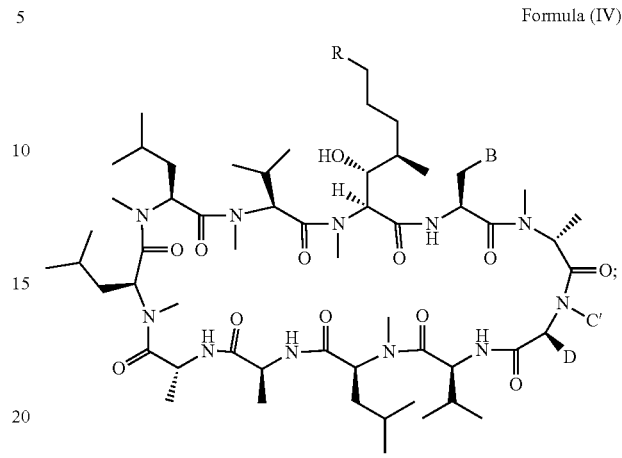

Formula (IV)

wherein B is at least one selected from the group consisting of —$CH_3$, —$CH_2CH_3$, —$CH(OH)CH_3$, —$CH(CH_3)_2$, and —$CH_2CH_2CH_3$;

C' is at least one selected from the group consisting of —H, —$CH_3$, —$CH_2CH_3$, and —$CH_2CH_2CH_3$;

D is at least one selected from the group consisting of —$CH_2CH(CH_3)_2$, —$CH_2C(OH)(CH_3)_2$, -$CH(CH_3)CH_2CH_3$, and —$CH_2CH_2$-[4-(2-$CH_3OCH_2CH_2$)-1-$R_3$];

$R_3$ is piperazinyl;

R is at least one selected from the group consisting of —$CH_2CH_2CH_2NH(C=O)CH_3$, —$CH_2CH_2CH_2COOH$, and the following groups:

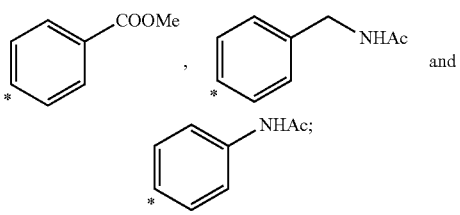

wherein the asterisk indicates the point of attachment.

The above method, combined with the methyleneization of flow chemistry, intermolecular olefin metathesis and diastereoselective hydrogenation, completes the diastereoselective synthesis of CRV431. Only 4 steps are required in the reaction process, and the yield can be as high as 34%, the product is easy to purify, realizes the large-scale preparation of cyclosporine 1,3 derivatives, and can quickly construct a molecular library of CRV431 derivatives, and promote the development of drugs with cyclosporine A as the backbone.

In one specific embodiment, B is —$CH_3$; C is —$CH_3$; and D is —$CH_2CH(CH_3)_2$.

In one specific embodiment, the olefin metathesis is carried out under the catalysis of the catalyst Hoveyda-Grubbs.

In one specific embodiment, the olefin metathesis refers to a reflux reaction using dichloromethane as a solvent. In another specific embodiment, the olefin metathesis refers to a microwave reaction at a temperature of 55° C. to 65° C. for 1 h to 2 h.

The followings are specific examples.

For the experimental parameters not specified in the following specific examples, priority is given to the guidelines given herein, and can also refer to the experimental manuals in the art or other experimental methods known in the art, or refer to the experimental conditions recommended by the manufacturer.

The raw materials and reagents involved in the following specific examples can be easily obtained or can be directly obtained commercially by those skilled in the art.

The abbreviations and corresponding Chinese names of the reagents involved in the examples:
CsA: cyclosporine A;
LDA: lithium diisopropylamide;
THF: tetrahydrofuran;
Hex: n-hexane;
DCM: dichloromethane;
MeOH: methanol.

Example 1 (Corresponding to Entry 9)

This example is a continuous method of synthesizing the cyclosporine derivative [methylene-sar]$^3$CsA 3, the steps are as follows, and the reaction flowchart is shown in FIG. 1:

1. Preparation stage: substrates CsA (0.055 M in THF) and LDA (0.25 M in THF/Hex), pump (HNP mzr-7208-hs-f S+SW), inline filter (Swagelok filter 40 μm), pressure relief valve (Swagelok proportional relief valves).

2. Start program:
2.1 The pumps were rinsed, including Pump A, Pump B, and Pump C, required for synthesis with dry tetrahydrofuran solution;
2.2 The pipeline of carbon dioxide gas was opened and the pressure of gas outlet was set to 2 Mpa to 5 Mpa;
2.3 The temperature setting channel was opened to reach −5° C.;
2.4 Pump A, Pump B, and Pump C were opened;
2.5 Once all temperatures reached equilibrium, i.e. −5° C., the solution inlet valves were switched in the following order: the inlet valve of Pump A was switched into the CsA solution, and the inlet valve of Pump B was switched into the LDA solution; then, the flow rate of Pump A was set to 1.0 mL/min, the flow rate of Pump B was set to 2.0 mL/min, and the flow rate of Pump C ($CO_2$ gas) was set to 10.3 mL/min, until the flowmeter read the required flow rate, then the system was equilibrated for about 5 min.

3. Start reaction stage: first, at −5° C., CsA and LDA were sucked through Pump A and Pump B respectively, mixed in the microchannel reactor 1, and reacted in the reactor for 54 s, then entered the microchannel reactor 2 to react with $CO_2$ for 12.2 s to produce an intermediate 2. The reaction solution containing the intermediate 2 was collected into a solution containing $ClCH_2OCOCl$ (0.5 M in THF, −50° C.), and stirring was continued overnight (9 h to 10 h)), during the stirring, the temperature of the system was gradually returned to room temperature.

4. Close program:
4.1 The outlet pipe was switched to the waste liquid bottle;
4.2 Pump A and Pump B were rinsed with dry tetrahydrofuran until no more product was generated, and about 3 to 5 reaction volumes were need for washing;
4.3 Pump A and Pump B were switched to ethanol and water respectively;
4.4 The thermostat was turned off;
4.5 The pumps was turned off;
4.6 The pipeline of carbon dioxide gas was closed.

During the whole reaction, the molar ratio of CsA, LDA and $CO_2$ was 1:9.1:8.4.

5. Post-treatment: water was added at 0° C., the pH of the reaction system was adjusted to neutral with 1 M dilute hydrochloric acid, concentrated under reduced pressure to remove tetrahydrofuran, then ethyl acetate (200 mL) was added, and the aqueous phase and organic phase were separated. The aqueous phase was extracted with ethyl acetate (3×200 mL), the combined organic phase was washed with saturated brine (2×200 mL), and then dried with anhydrous sodium sulfate. After filtration, concentrated under reduced pressure to remove the organic solvent, then the remaining crude product was separated and purified by silica gel column chromatography (DCM/MeOH: 20:1). 2.14 g of [methylene-sar]$^3$CsA 3 as a pale yellow solid was obtained.

The reaction was monitored by 0.25 mm thin layer chromatography silica gel plate (60F-254). The NMR characterization was measured by Brüker Advance 500 ($^1$H: 500 MHz, $^{13}$C: 125 MHz) instrument. The deuterated reagents for calibrations were: $CDCl_3$: $^1$H NMR=7.26 ppm, $^{13}$C NMR=77.0 ppm; $C_6D_6$: $^1$H NMR=7.15 ppm, $^{13}$C NMR=128.0 ppm). The high resolution mass spectrum was measured by the Bruker Apex IV RTMS instrument.

Compound 3:

$R_f$=0.40 (silica gel, DCM/MeOH: 20:1, PMA);

$^1$H NMR (500 MHz, $CDCl_3$) δ (ppm): 7.90 (d, J=9.5 Hz, 1H), 7.62 (d, J=7.3 Hz, 1H), 7.55 (d, J=8.7 Hz, 1H), 7.13 (d, J=7.8 Hz, 1H), 5.62 (dd, J=11.1, 4.3 Hz, 1H), 5.39-5.27 (m, 3H), 5.22 (s, 1H), 5.16 (dd, J=12.1, 3.8 Hz, 1H), 5.11-4.95 (m, 5H), 4.78 (t, J=7.2 Hz, 1H), 4.67 (t, J=9.2 Hz, 1H), 4.45 (t, J=7.3 Hz, 1H), 4.07 (q, J=7.1 Hz, 1H), 3.90 (t, J=6.8 Hz, 1H), 3.43 (s, 6H), 3.18 (s, 3H), 3.09 (s, 3H), 3.02 (s, 3H), 2.65 (s, 6H), 2.32-2.22 (m, 2H), 2.15-2.04 (m, 3H), 2.02-1.92 (m, 3H), 1.75-1.52 (m, 10H), 1.46 (d, J=6.6 Hz, 3H), 1.32 (d, J=7.4 Hz, 3H), 1.23-1.19 (m, 4H), 0.97 (t, J=5.0 Hz, 8H), 0.95-0.90 (in, 10H), 0.88 (d, J=6.6 Hz, 4H), 0.85-0.79 (m, 17H), 0.72 (d, J=6.7 Hz, 3H);

$^{13}$C NMR (125 MHz, $CDCl_3$) δ: 173.61, 173.51, 173.37, 173.22, 171.40, 171.28, 170.42, 170.30, 170.05, 169.97, 168.96, 143.45, 129.62, 126.22, 107.50, 73.95, 60.40, 58.68, 58.05, 57.53, 55.46, 55.12, 55.05, 49.38, 48.82, 48.32, 45.20, 40.91, 39.02, 37.95, 37.15, 35.67, 35.57, 35.13, 33.88, 33.62, 31.42, 31.34, 29.77, 29.65, 28.71, 25.36, 25.05, 25.01, 24.67, 24.61, 23.86, 23.69, 23.65, 23.51, 23.08, 22.12, 21.80, 21.02, 20.01, 19.51, 18.78, 18.54, 18.11, 17.91, 16.67, 16.22, 14.20, 9.82;

HRMS (ESI) m/z calcd for $C_{63}H_{112}N_{11}O_{12}^+$ [M+H]$^+$: 1214.8486, found: 1214.8520.

Example 2

Figure 2:
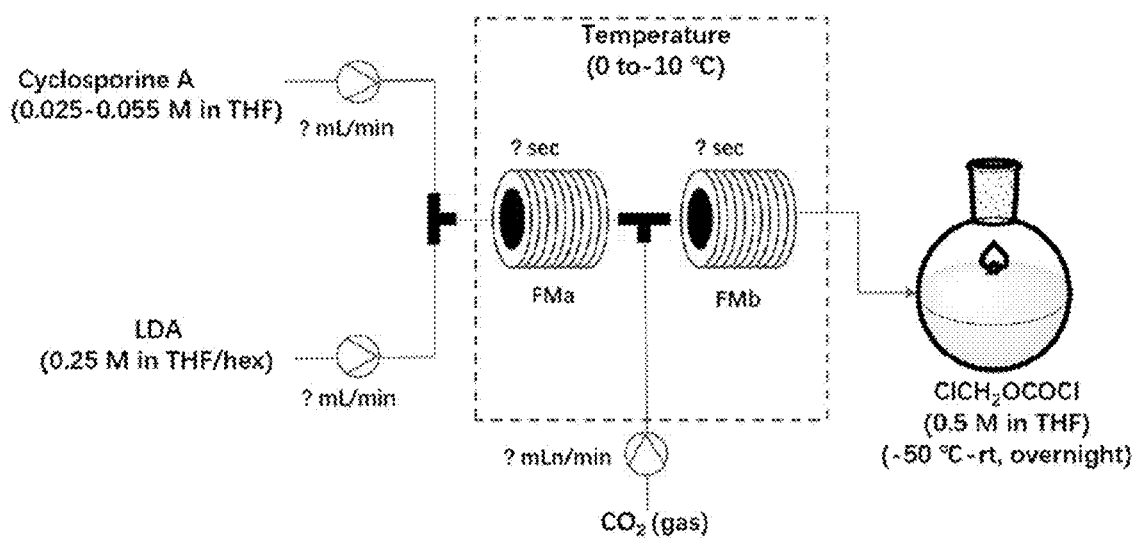
FIG. 2 is a connection diagram of the continuous flow reaction of the continuous method of synthesizing the cyclosporine derivative [methylene-sar]$^3$CsA 3 according to Example 2.

In this example, the reaction conditions of the continuous method of synthesizing the cyclosporine derivative [methylene-sar]$^3$CsA 3 was investigated, and the flowchart of condition screening is shown in FIG. 2.

Reaction conditions: substrate CsA (0.025 M in THF for entry 1 to 8, 0.055 M in THF for entry 9); the concentration (2.0 M in THF/Hex) of LDA solution. The flow rate of carbon dioxide gas was the value under normal pressure conditions, and the remaining reaction steps were the same as that in Example 1 except for the changed parameters. The ratio of the substrate CsA to the product 2 was determined by the results of LCMS analysis. The results are shown in Table 1 below

TABLE 1

Optimization for the flow rates of alkali and carbon dioxide in continuous flow reaction

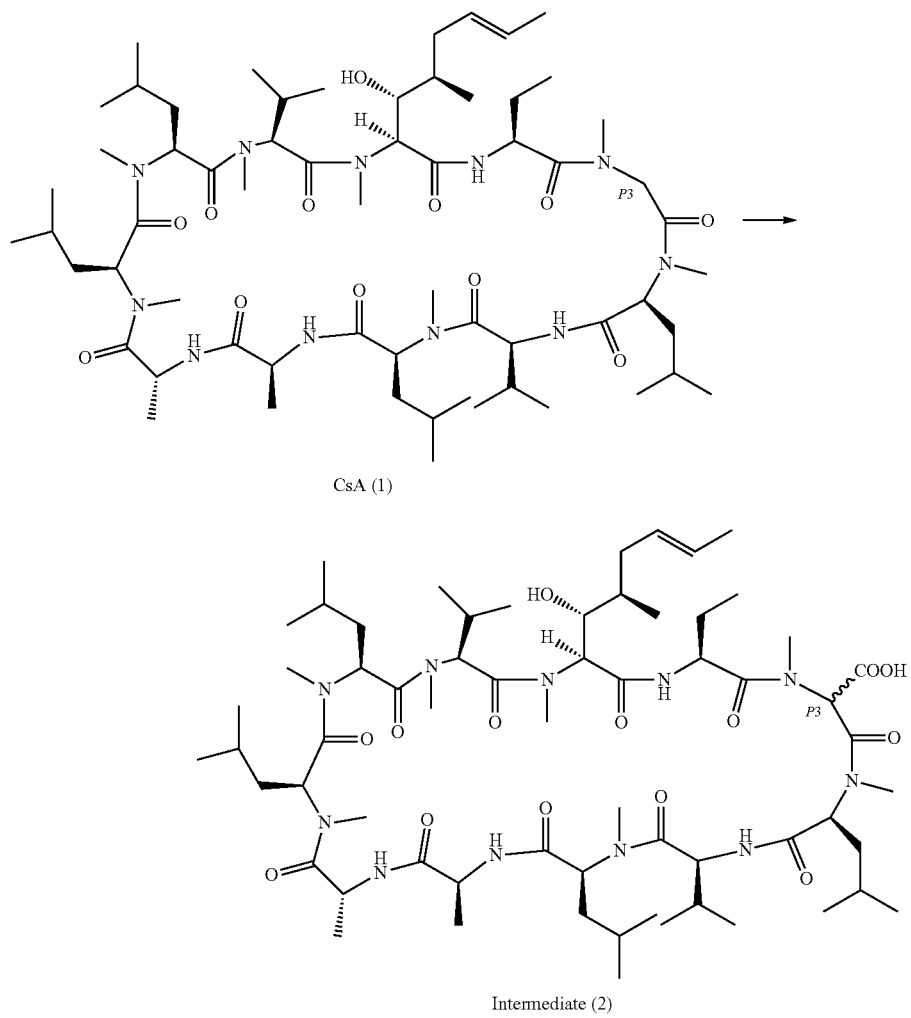

CsA (1)

Intermediate (2)

| Entry | Molar ratio CsA/LDA/ $CO_2$ | Flow rate A mL/min | Flow rate B mL/min | Flow rate C mL/min | Back pressure (psi) | Temperature ° C. | Resident time (sec) FMa + FMb | Substrate/ product (1/2) |
|---|---|---|---|---|---|---|---|---|
| 1 | 1:10:10 | 1.5 | 1.5 | 8.4 | 0 | −5 | 54 ± 14.2 | 27/73 |
| 2 | 1:10:20 | 1.5 | 1.5 | 16.8 | 0 | −5 | 54 ± 3.0 | 82/18 |
| 3 | 1:6:20 | 1.5 | 0.9 | 16.8 | 0 | −5 | 67.5 ± 8.4 | 100/0 |
| 4 | 1:8:20 | 1.5 | 1.2 | 16.8 | 0 | −5 | 60 ± 8.3 | 68/32 |
| 5 | 1:10:20 | 1.5 | 1.5 | 16.8 | 12.5 | −5 | 54 ± 8.2 | 40/60 |
| 6 | 1:10:10 | 1.0 | 1.0 | 6.3 | 0 | 0 | 81 ± 19.5 | 49/51 |
| 7 | 1:10:10 | 1.5 | 1.5 | 8.4 | 0 | 0 | 54 ± 14 | 53/47 |
| 8 | 1:10:12.3 | 1.5 | 1.5 | 10.3 | 0 | −5 | 54 ± 12.2 | 0/100 |
| 9 | 1:9.1:8.4 | 1.0 | 2.0 | 10.3 | 0 | −5 | 54 ± 12.2 | 0/100 |

The entry 9 corresponds to the preparation method of Example 1.

Example 3

In this example, the influence of different alkalies and solvents on the continuous method of synthesizing the cyclosporine derivative [methylene-sar]³CsA 3 was investi- gated. The process changes shown in Table 2 below were made on the basis of Example 1 (that is, the remaining reaction steps are the same as that in Example 1 except for the changed parameters). The results showed that in addition to LDA, both LiHMDS and NaHMDS can obtain better results, and the result of LiHMDS can be comparable to that of LDA, and the reaction in the solvent 2-MeTHF can also be carried out.

TABLE 2

Screening of the alkali and solvent in continuous flow reaction

| Entry | CsA (A) | Base (B) | CO$_2$ (C) | Molar ratio (CsA/Base/CO$_2$) | Temperature | Substrate/product (1/2) |
|---|---|---|---|---|---|---|
| 10 | 0.01 mmol in THF (1.5 mL/min) | LiHMDS 0.1 mmol in THF (3.0 mL/min) | 8.4 mL/min | 1:20:25 | −5 | 67% |
| 11 | 0.01 mmol in THF (1.5 mL/min) | LiHMDS 0.1 mmol in THF (1.5 mL/min) | 5.1 mL/min | 1:10:15 | −5 | 75% |
| 12 | 0.01 mmol in THF (1.5 mL/min) | LiHMDS 0.1 mmol in THF (1.5 mL/min) | 5.1 mL/min | 1:15:20 | 0 | 75% |
| 13 | 0.01 mmol in THF (1.5 mL/min) | LiHMDS 0.1 mmol in THF (1.5 mL/min) | 5.1 mL/min | 1:10:15 | 10 | 61% |
| 14 | 0.01 mmol in THF (1.5 mL/min) | LiHMDS 0.1 mmol in THF (1.5 mL/min) | 5.1 mL/min | 1:10:15 | 20 | 71% |
| 15 | 0.01 mmol in THF (1.5 mL/min) | LiHMDS 0.1 mmol in THF (1.5 mL/min) | 5.1 mL/min | 1:10:15 | 30 | 67% |
| 16 | 0.01 mmol in THF (1.0 mL/min) | LiHMDS 0.2 mmol in THF (1.0 mL/min) | 6.7 mL/min | 1:20:30 | −5 | 92% |
| 17 | 0.01 mmol in 2-MeTHF (1.5 mL/min) | LDA 0.2 mmol in 2-MeTHF (1.5 mL/min) | 5.1 mL/min | 1:10:15 | −5 | 47% |
| 18 | 0.02 mmol in THF (1 mL/min) | NaHMDS 0.25 mmol in THF (2 mL/min) | 10.3 mL/min | 1:25:23 | −5 | 44% |

Example 4

This example shows the method of synthesizing the cyclosporine 1,3-position derivative (CRV431). The cyclosporine derivative [methylene-sar]$^3$CsA 3 prepared in Example 1 was used as the raw material (compound 3). The steps are as follows

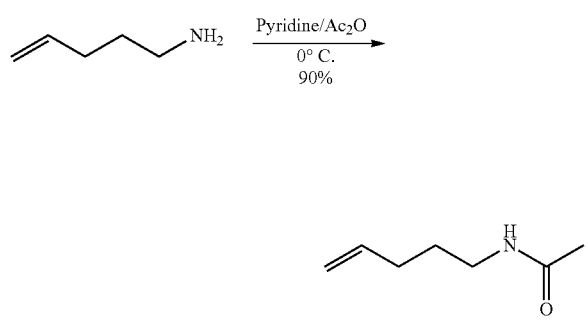

The compound 4-alkenylpentylamine (608 mg, 5 mmol, 1 equiv.) was added to a dry reaction flask (50 mL), and acetic anhydride (5 mL) and pyridine (10 mL) were added at 0° C. The reaction was stirred at room temperature for 5 hours. After the substrate was consumed as monitored by TLC, water (10 mL) was added to the reaction system at 0° C. to quench the reaction, then ethyl acetate (15 mL) was added, and then the aqueous phase and the organic phase were separated, the aqueous phase was extracted with ethyl acetate (3×15), and the combined organic phase was washed with saturated brine (2×20 mL) and then dried with anhydrous sodium sulfate. After filtration, the organic solvent was removed by concentration under reduced pressure, and the remaining crude product was separated and purified by silica gel column chromatography (n-hexane: ethyl acetate=10:1 to 2:1). Then, 570 mg of N-acetyl-4-enylpentylamine as a colorless oily liquid was obtained with a yield of 90%.

$^1$H NMR (500 MHz, CDCl$_3$) δ: 6.08 (s, 1H), 5.81-5.71 (m, 1H), 5.02-4.91 (m, 2H), 3.20 (q, 2H), 2.08-2.02 (m, 2H), 1.92 (s, 3H), 1.60-1.53 (m, 2H).

HRMS (ESI) m/z calcd for C$_7$H$_{14}$NO$^+$ ([M+H]$^+$): 128.1070 found: 128.1081.

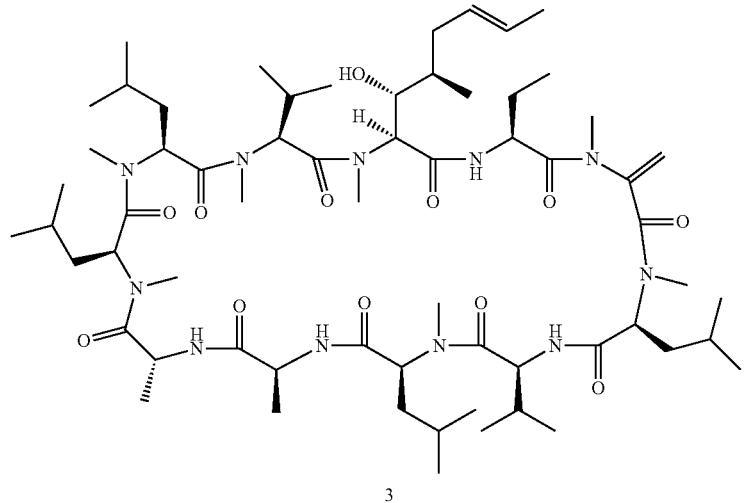
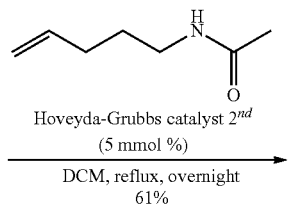

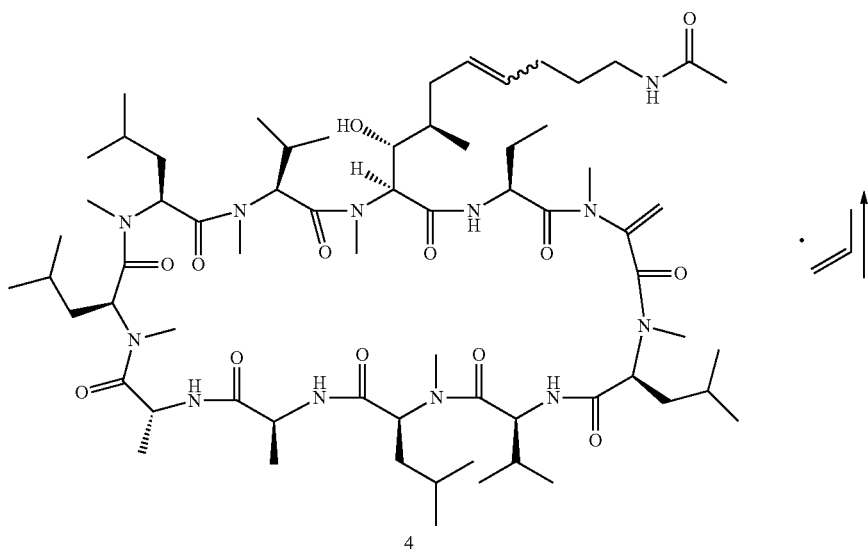

The compound 3 (834.9 mg, 0.68 nmol, 1.0 equiv.) and N-acetyl-4-enylpentylamine (87.4 mg, 0.68 mmol, 1.0 equiv.) were dissolved in dry dichloromethane (5 mL), and Hoveyda-Grubbs catalyst $2^{nd}$ (21.6 mg, 0.014 mmol, 0.05 equiv.) was added, and then the reaction system was refluxed overnight. After the completion of the reaction, the reaction system was cooled to room temperature, and the organic solvent was removed by concentration under reduced pressure, then the remaining crude product was separated and purified by silica gel column chromatography (methyl tert-butyl ether:methanol=20:1). Then, 543 mg of a compound 4 as a white solid was obtained with a yield of 61%.

$^1$H NMR (500 MHz, CDCl$_3$) δ 8.04 (d, J=9.5 Hz, 1H), 7.77 (d, J=8.9 Hz, 1H), 7.65 (d, J=7.2 Hz, 1H), 7.23 (d, J=7.9 Hz, 1H), 6.91 (s, 1H), 3.51 (s, 3H), 3.45 (s, 3), 3.20 (s, 4H), 3.12 (s, 3H), 3.07 (s, 3H), 2.66 (s, 6H), 2.01 (s, 3H).

Figure 3:
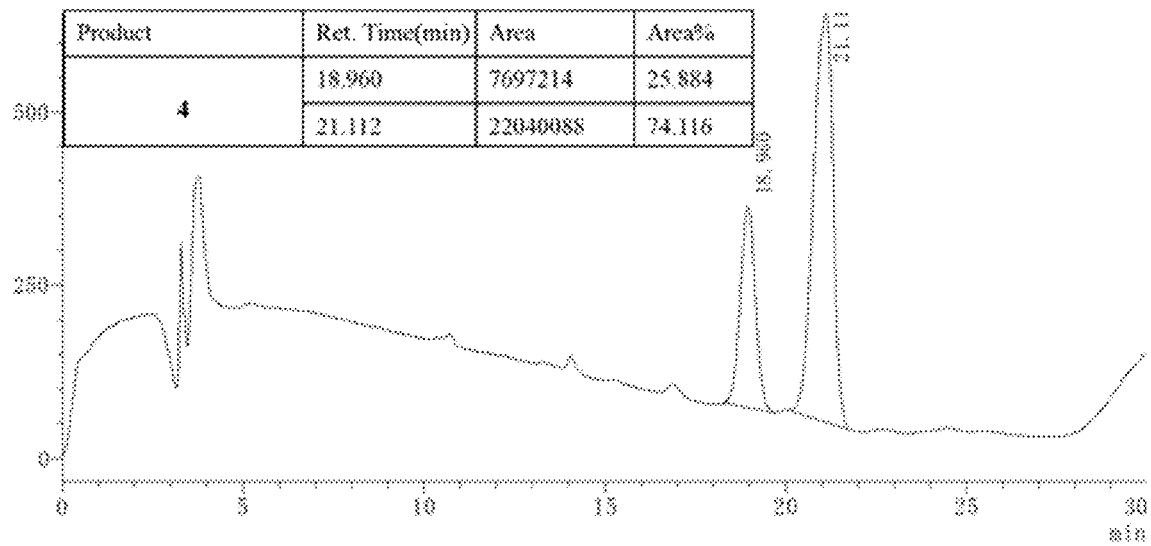
FIG. 3 is an HPLC diagram of the compound 4 prepared according to Example 4.

The compound 4 was analyzed by HPLC, and the spectrum thereof is shown in FIG. 3: mobile phase (A: 0.1% solution of CF$_3$COOH in water, B: acetonitrile), flow rate: 0.5 mL/min; elution gradient: 0 min-15 min, 50% B to 90% B; 15 min-22 min, 90% B; 22 min-25 min, 90% B to 50% B; 25 min-30 min, 50% B; UV detection wavelength: λ=214 nm; chromatographic column: Aligent Poroshell 120 SB-C18 column (2.7 μm particle size, 4.6 mm×150 mm); column temperature: 70° C.

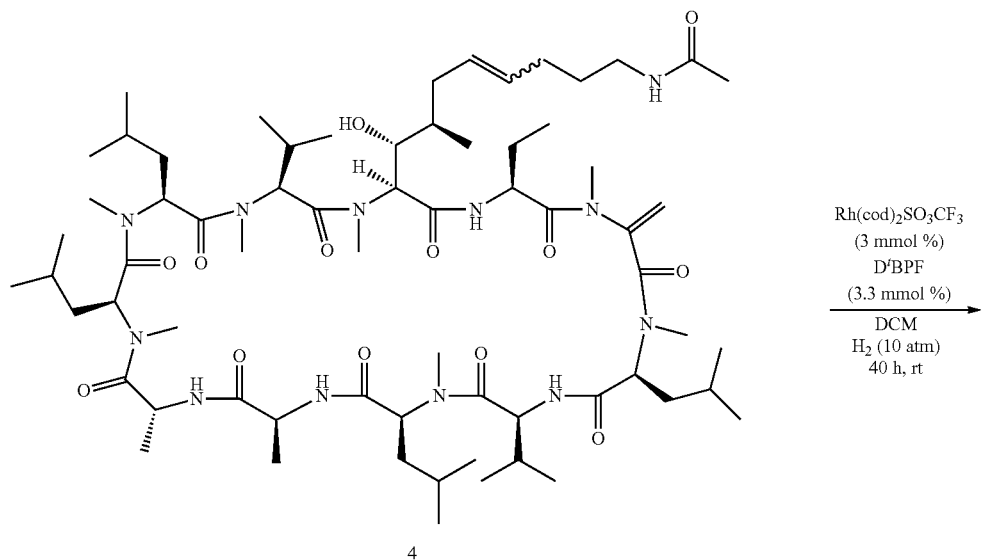

4

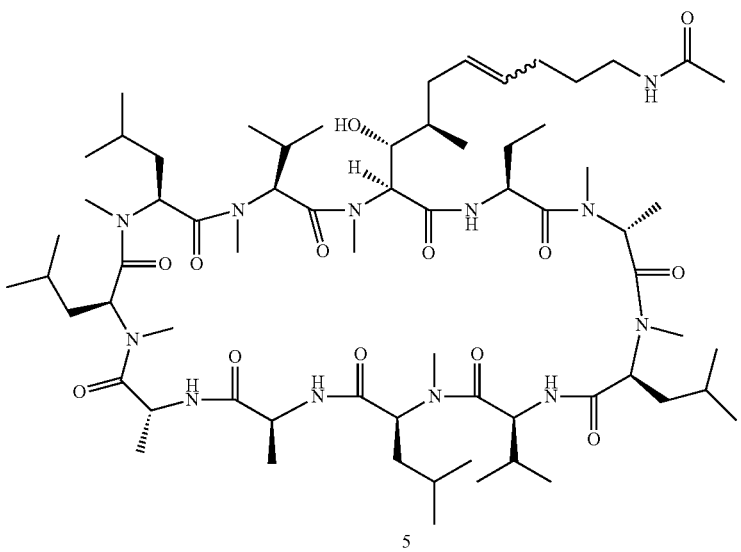

5

In a glovebox filled with argon, the compound 4 (104 mg, 0.08 mmol, 1 equiv.) was dissolved in dry DCM (5 mL), and [Rh(cod)₂]OTf (1.1 mg, 0.0024 mmol, 0.03 equiv. and D'BPF (1.2 mg, 0.0044 mmol, 0.033 equiv.) were added, then the reaction system was carefully transferred into an autoclave, stirred in advance for 5 minutes, and then the gas in the autoclave was replaced with high-pressure hydrogen for three times. 10 atm of hydrogen was slowly charged, and then the reaction was stirred at 35° C. for 40 hours. After the reaction was completed, the hydrogen in the autoclave was slowly and carefully released in a fume cupboard, then the reaction still was opened, and the reaction system was concentrated under vacuum and reduced pressure, and then dissolved M MeOH and filtered with diatomite. The resulting product 5 was directly carried to the next step without purification.

Figure 4:
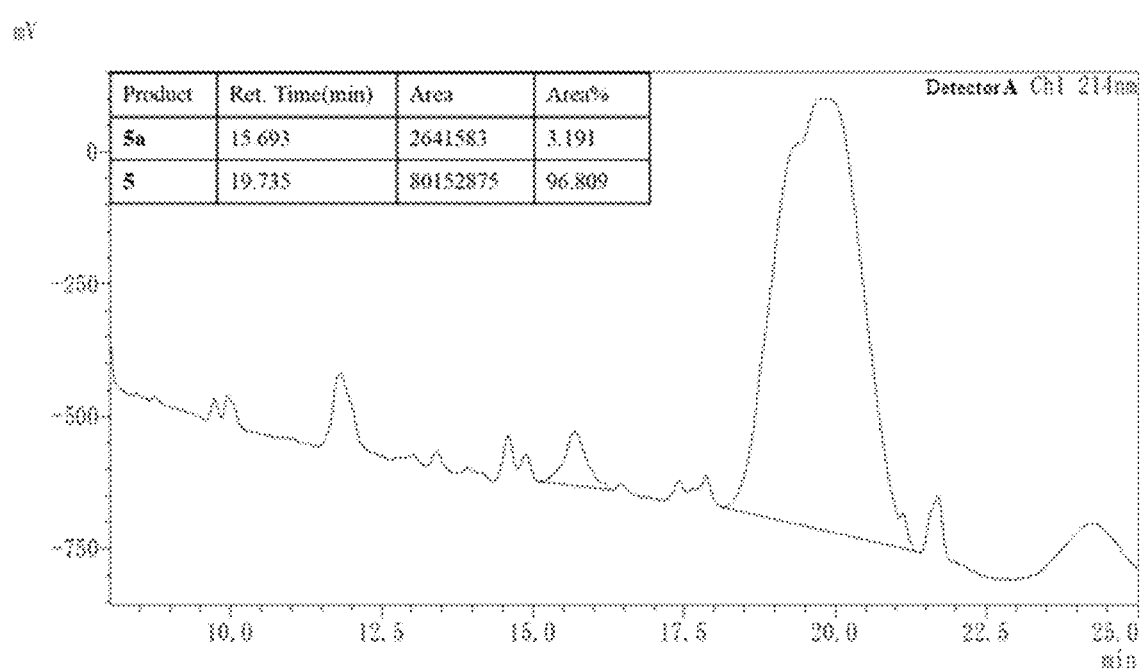
FIG. 4 is an HPLC diagram of product 5 prepared according to Example 4.

A 3-position L configuration isomer 5a of a compound 5 will be produced during the reaction. After the reaction was completed, by analyzing the crude product, it can be determined that the ratio of the product 5 to the by-product reactant 5n was about 97:3, and the spectrum is shown in FIG. 4.

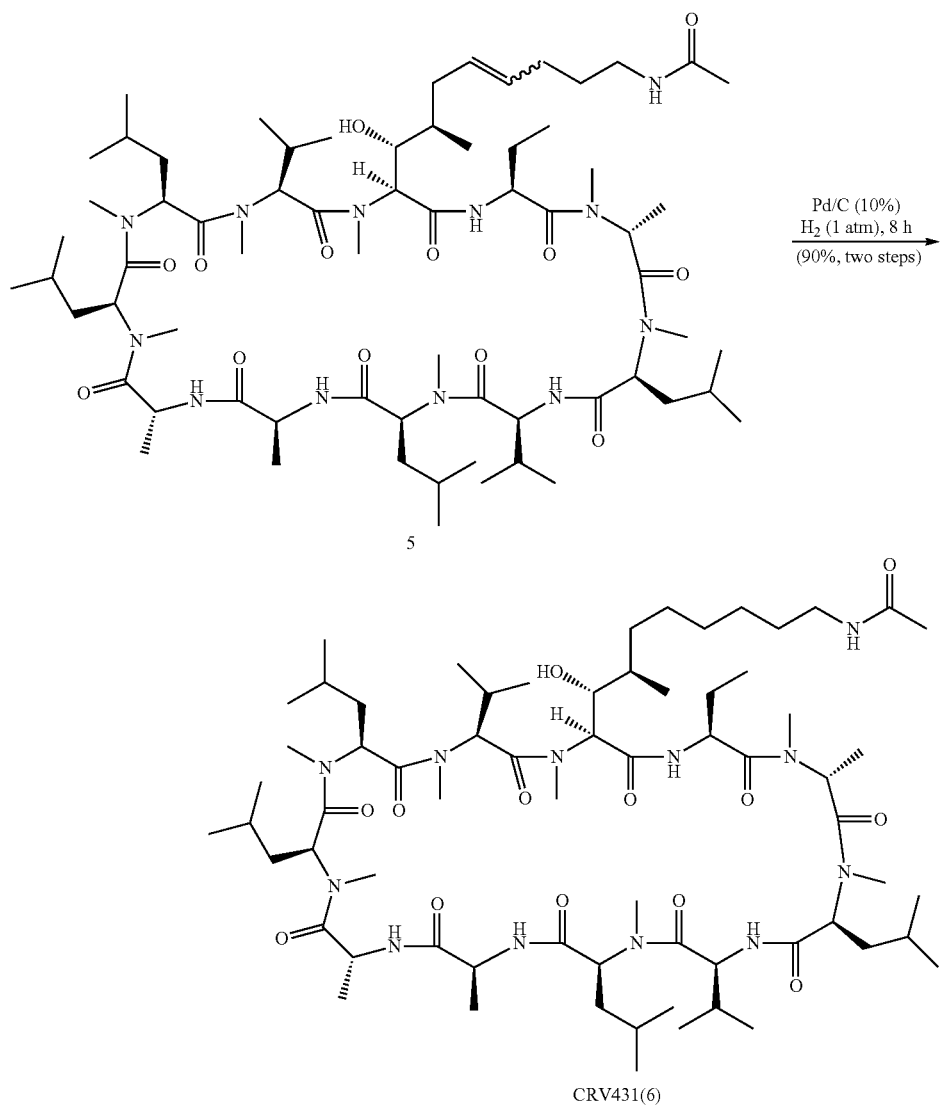

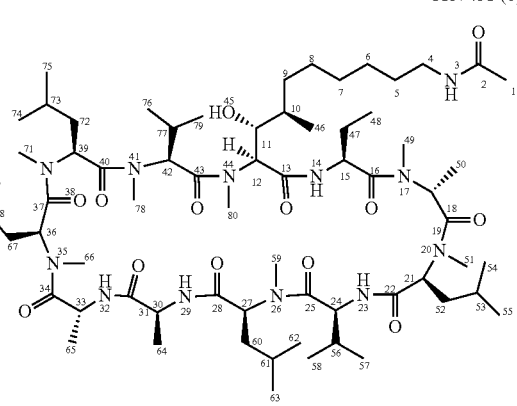

CRV431 (6)

To the above MeOH solution containing the product 5, 10% Pd/C (10 mg) was added, the reaction system was replaced with a hydrogen balloon for 3 times, and the reaction was stirred overnight at room temperature. The reaction was detected by LCMS. After the reaction was completed, the reaction system was concentrated under vacuum and reduced pressure, and the crude product was filtered through diatomite to obtain 94 mg of CRV431 (6) as a pale yellow solid with a yield of 90%.

Figure 5:
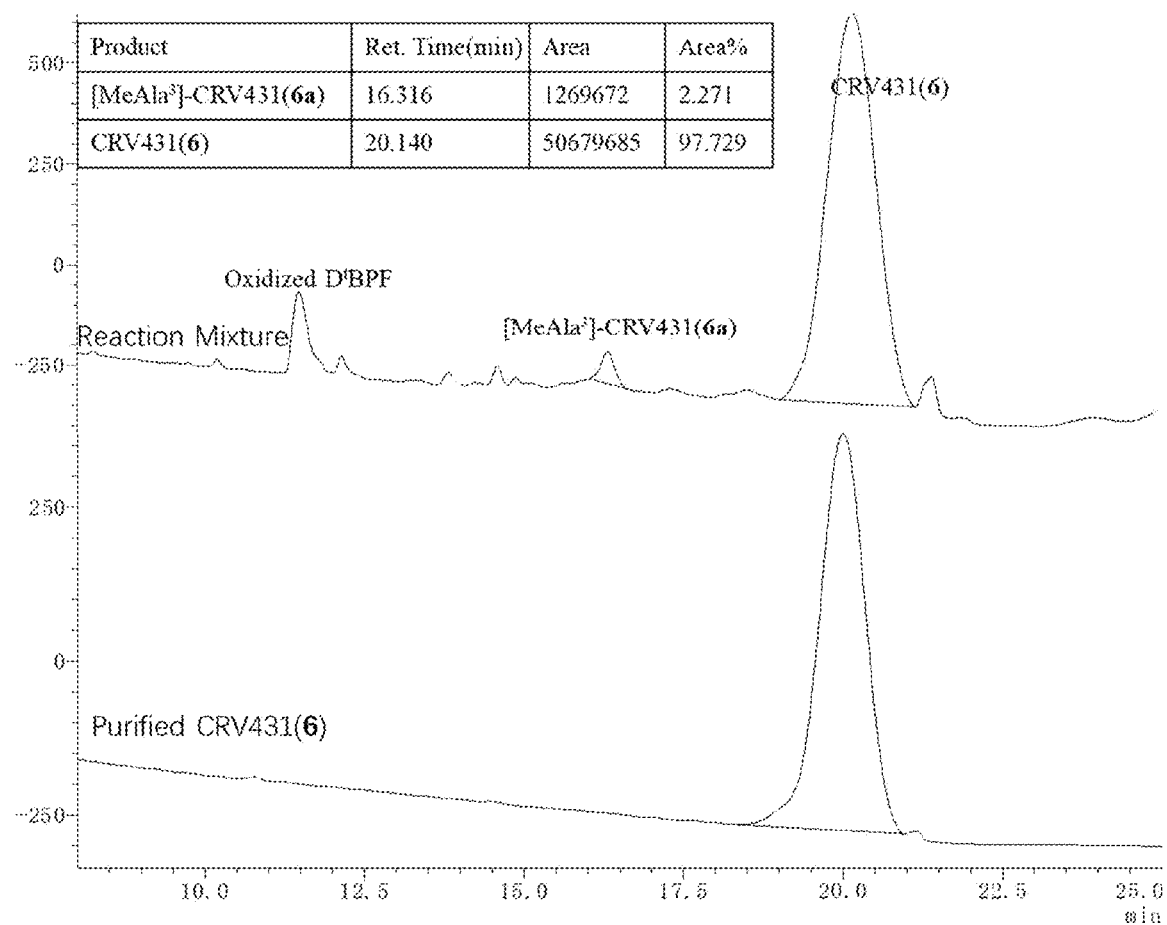
FIG. 5 is an HPLC diagram of the product 6 prepared according to Example 4.

After the reaction was completed, the by-product 6a of the 3-position L configuration and the CRV431 (6) were analyzed by HPLC, the ratio was about 3:97, and the spectrum thereof is shown in FIG. 5: mobile phase (A: 0.1% solution of $CF_3COOH$ in water, B: acetonitrile), flow rate: 0.5 mL/min; elution gradient: 0 min-15 min, 50% B to 90% B; 15 min-22 min, 90% B; 22 min-25 min, 90% B to 50% B; 25 min-30 min, 50% B; UV detection wavelength: $\lambda$=214 nm; chromatographic column: Aligent Poroshell 120 SB-C18 column (2.7 μm particle size, 4.6 mm×150 mm); column temperature: 70° C. The purified CRV431 (6):

HRMS (ESI) m/z calcd for $C_{67}H_{122}N_{12}O_{13}Na$ $([M+Na]^+)$: 1325.91465; found: 1325.91541.

$^1$H NMR (600 MHz, $CDCl_3$) δ 8.01 (d, J=9.9 Hz, 1H, 14), 7.72 (d, J=7.4 Hz, 1H, 29), 7.53 (d, J=8.4 Hz, 1H, 23), 7.23 (d, J=7.9 Hz, 1H, 32), 6.25 (s, 1H, 3), 5.70 (dd, J=11.0, 4.2

Hz, 1H, 36), 5.39 (d, J=7.0 Hz, 1H, 12), 5.29 (dd, J=12.0, 3.7 Hz, 1H, 21), 5.11 (d, J=10.9 Hz, 1H, 42), 5.03 (ddd, J=15.6, 12.0, 6.2 Hz, 3H, 39, 15 and 27), 4.94 (q, J=7.2 Hz, 1H, 18), 4.83 (p, J=6.9 Hz, 1H, 33), 4.67 (t, J=9.1 Hz, 1H, 24), 4.51 (p, J=7.2 Hz, 1H, 30), 3.76 (t, J=6.3 Hz, 1H, 1.1), 3.50 (s, 3H, N—CH₃), 3.41 (s, 1H, 45), 3.27 (s, 3H, N—CH₃), 3.25 (s, 3H, Cl₃), 3.23 (d, J=6.6 Hz, 2H, 4), 3.12 (s, 3H, N—CH₃), 3.09 (s, 3H, N—CH₃), 2.70 (s, 3H, N—CH₃), 2.68 (s, 3H, N—CH₃), 2.47-2.40 (m, 1H, 56), 2.18-2.09 (m, 3H, 67, 77 and 60), 2.03 (d, J=7.51 Hz, 1H, 72), 2.00 (s, 3H, 1), 1.94 (ddd, J=14.5, 10.6, 3.8 Hz, 1H, 52), 1.80 (s, 1H, 68), 1.69 (d, J=6.6 Hz, 2H, 47 and 52), 1.64 (dd, J=11.8, 3.9 Hz, 2H, 47 and 9), 1.58-1.53 (m, 1H, 10), 1.52-1.44 (m, 2H, 5 and 53), 1.41 (d, J=7.3 Hz, 5H, 5, 50 and 61), 1.34 (d, J=7.2 Hz, 5H, 64, 73 and 60), 1.31 (d, J=6.3 Hz, 3H, 8 and 72), 1.26 (d, J=6.8 Hz, 5H, 6 and 65), 1.22-1.19 (m, 1H, 67), 1.15 (d, J=7.2 Hz, 2H, 8 and 7), 1.08 (d, J=6.5 Hz, 3H, 57), 1.03 (d, J=6.6 Hz, 3H, 74), 1.01 (d, J=6.5 Hz, 6H, 75 and 69), 0.95 (t, J=6.7 Hz, 10H, 9, 78, 62 and 54), 0.90-0.87 (m, 6H, 58 and 79), 0.85 (t, J=7.3 Hz, 9H, 48, 55 and 70), 0.81 (d, J=6.6 Hz, 3H, 63) 0.79 (d, J=6.7 Hz, 3H, 46).

¹³C NMR (151 MHz, CDCl₃) δ 175.44, 174.25, 173.66, 173.64, 173.54, 171.57, 171.12, 170.45, 170.43, 170.30, 170.20, 170.11, 74.79, 59.05, 58.00, 57.56, 55.36, 55.11, 50.99, 49.64, 48.51, 48.10, 45.05, 40.53, 39.54, 39.01, 37.68, 35.95, 35.72, 33.68, 31.81, 31.59, 31.56, 31.33, 30.86, 30.47, 29.92, 29.79, 29.54, 29.22, 27.25, 27.07, 25.22, 25.12, 25.01, 24.65, 24.40, 24.00, 23.81, 23.74, 23.63, 23.56, 23.29, 21.84, 21.73, 21.16, 20.42, 19.92, 18.72, 18.28, 18.10, 17.49, 15.79, 13.91, 9.99.

Example 5

This example shows the method of synthesizing the CRV431 derivative. The cyclosporine derivative [methylene-sar]³CsA 3 prepared in Example 1 was used as the raw material (compound 3). The steps are as follows:

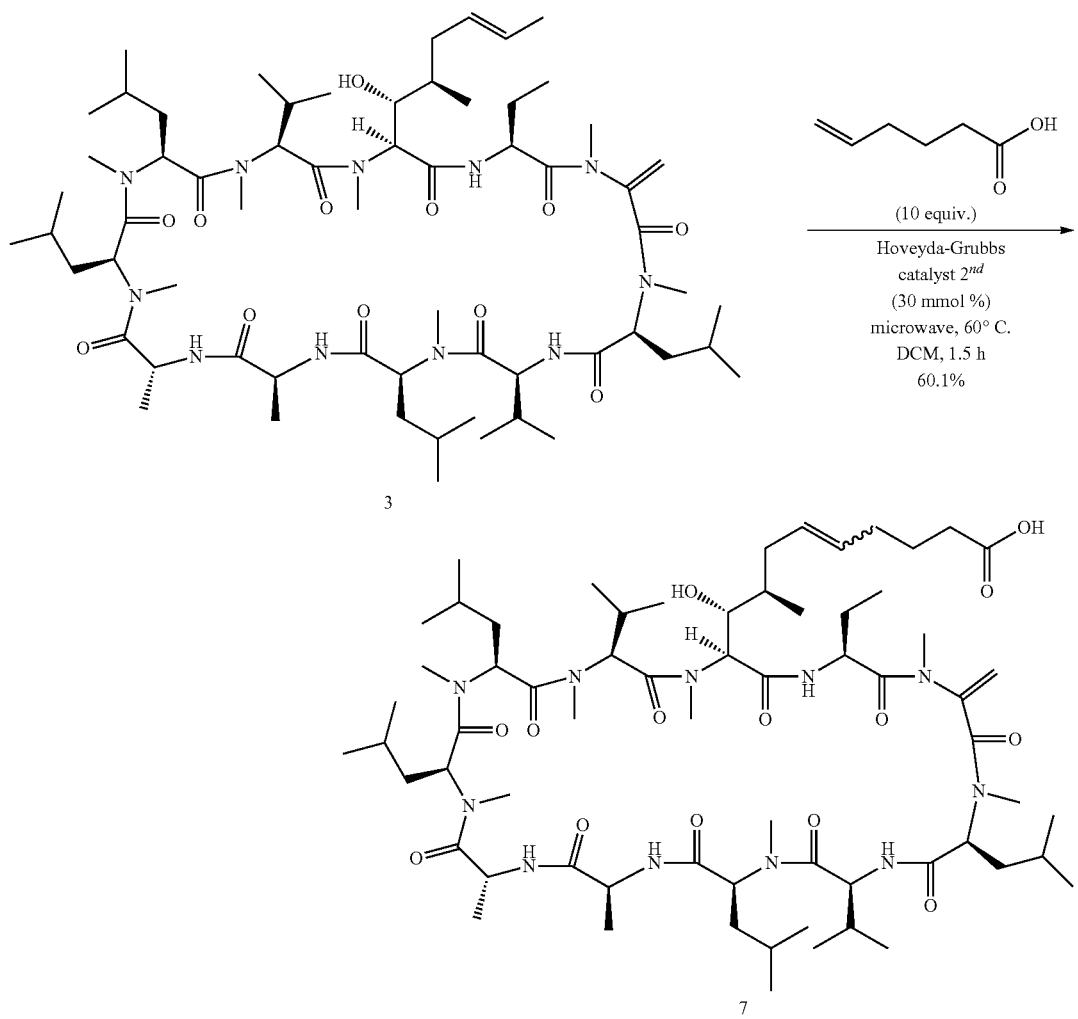

The compound 3 (40 mg, 0.033 mmol, 1 equiv.) was added to the special reaction flask for Biotage® microwave reactor, and dichloromethane (4 mL) was added for dissolving, then in the air, the substrate 5-alkenylhexanoic acid (38 mg, 0.33 mmol, 10 equiv.) and Hoveyda-Grubbs catalyst 2$^{nd}$ (6.2 mg, 0.0099 mmol, 30 mol %) were added, the reaction flask was sealed and placed in the Biotage® Initiator+ microwave reactor at 60° C. to react for 1.5 hours. After the completion of the reaction, the reaction system was cooled to room temperature, and the organic solvent was removed by concentration under reduced pressure, then the remaining crude product was separated and purified by silica gel column chromatography (methyl tert-butyl ether:methanol=20:1), and the obtained mixture was further purified by semi-preparative HPLC. Then, 25.5 mg of white solid 7 was obtained with a yield of 60.1% (it can be roughly calculated based on the peak area of the LC that E/Z: 4.2:1).

Compound 7 $R_f$=0.30 (silica gel, TBME/MeOH=30:1, PMA); The $^1$H NMR of E-configuration of 6: $^1$H NMR (400 MHz, CDCl$_3$) δ 8.04 (d, J=9.4 Hz, 1H), 7.72 (d, J=8.8 Hz, 1H), 7.62 (d, J=7.4 Hz, 1H), 7.22 (d, d=8.0 Hz, 1H), 3.48 (s, 3H), 3.45 (s, 3H), 3.21 (s, 3H), 3.14 (s, 3H), 3.06 (s, 3H), 2.68 (d, J=2.2 Hz, 6H). $^1$HNMR of Z-configuration of 7: $^1$H NMR (400 MHz, CDCl$_3$) δ 7.82 (dd, J=8.8, 5.2 Hz, 2H) 7.43 (d, J=7.5 Hz, 1H), 7.18 (d, J=7.9 Hz, 1H), 3.51 (s, 3H), 3.46 (s, 3H), 3.23 (s, 3H), 3.10 (s, 3H), 3.09 (s, 3H), 2.70 (d, J=1.5 Hz, 6H). HRMS (ESI) m/z calcd for $C_{66}H_{115}N_{11}NaO_{14}^+$ ([M+Na]$^+$): 1308.8517; found: 1308.85168.

at room temperature and reacted for 7 hours, the hydrogen in the autoclave was slowly and carefully released in a fume cupboard, then the reaction still was opened, and the reaction solution was taken out, then filtered with diatomite, and then directly carried to the next step without purification.

The above reaction system was protected by argon, 10% Pd/C (20 mg) was added at 0° C., and the reaction system was replaced with a hydrogen balloon for 3 times, then the reaction was stirred overnight at room temperature. The reaction was detected by LCMS, After the reaction was completed, the reaction solution was filtered with diatomite, and the reaction solution was concentrated under vacuum and reduced pressure without purification, then 16.3 mg of pale yellow solid 8 was obtained with a yield of 82%.

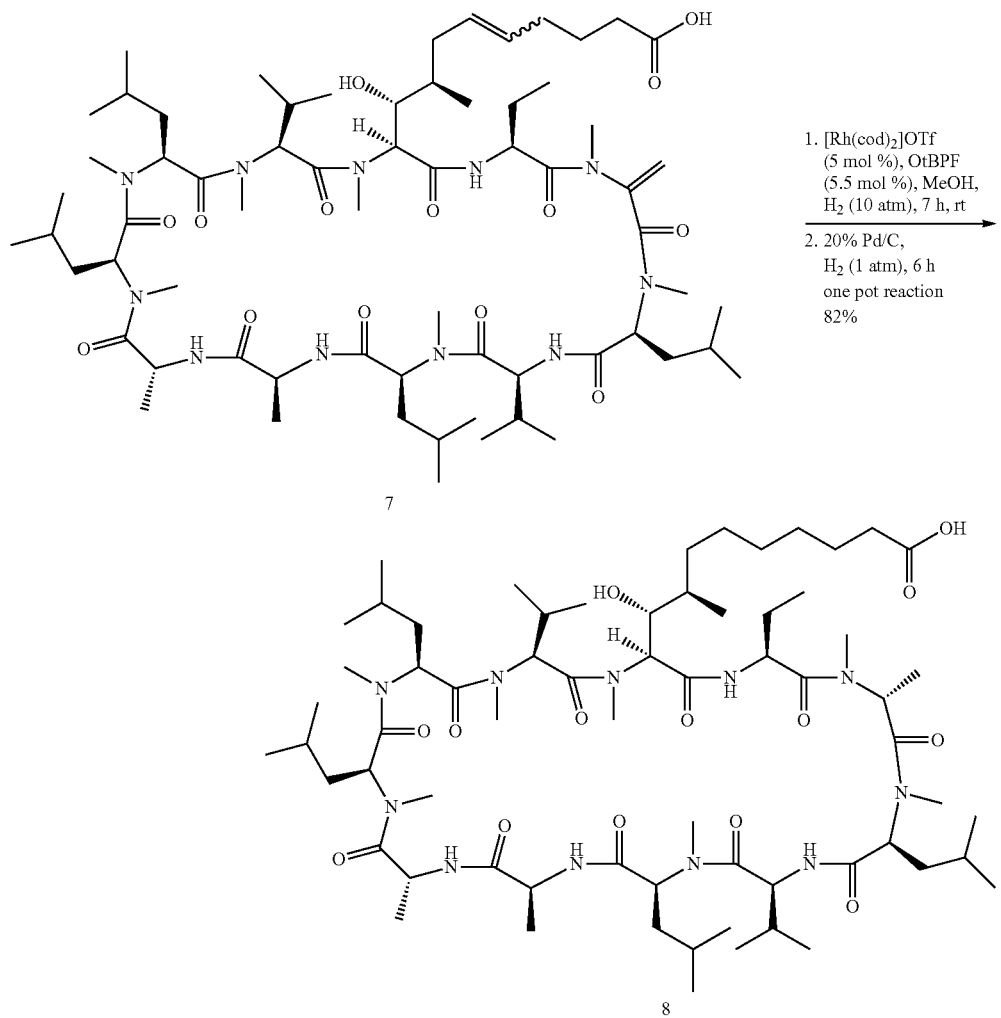

In a glove box filled with argon, [Rh(cod)$_2$]OTf (3.8 mg, 0.008 mmol) and D/BPF (4.2 mg, 0.0088 mmol) were weighed with a molar ratio of 1:1.1, and dissolved in dry methanol (1 mL)), then stirred at room temperature for about 10 minutes. A catalyst (97 μL, 5 mol %) was taken by a microsyringe into a reaction flask containing the substrate 7 (10 mg, 0.0155 (nmol, 1 equiv.), and dry methanol (1 mL) solvent was added. After replacing the gas in the reaction flask with a hydrogen balloon for three times, 10 atm of hydrogen was slowly charged, then the reaction was stirred Compound 8: $H_f$=0.30 (silica gel, TBME/MeOH=30:1, PMA);

$^1$H NMR (500 MHz, CDCl$_3$) δ 7.82 (d, J=9.9 Hz, 1H), 7.57 (dd, J=16.2, 7.8 Hz, 2H), 7.15 (d, J=8.0 Hz, 1H), 3.50 (s, 3H), 3.26 (s, 3H), 3.23 (s, 3H), 3.08 (s, 6H), 2.71 (s, 3H), 2.69 (s, 3H).

HRMS (ESI) m/z calcd for $C_{66}H_{119}N_{11}NaO_{14}^+$ ([M+Na]$^+$): 1312.8830, found: 1312.88342.

Example 6

This example shows the method of synthesizing the CRV431 derivative. The cyclosporine derivative [methylene-sar]³CsA 3 prepared in Example 1 was used as the raw material (compound 3). The steps are as follows:

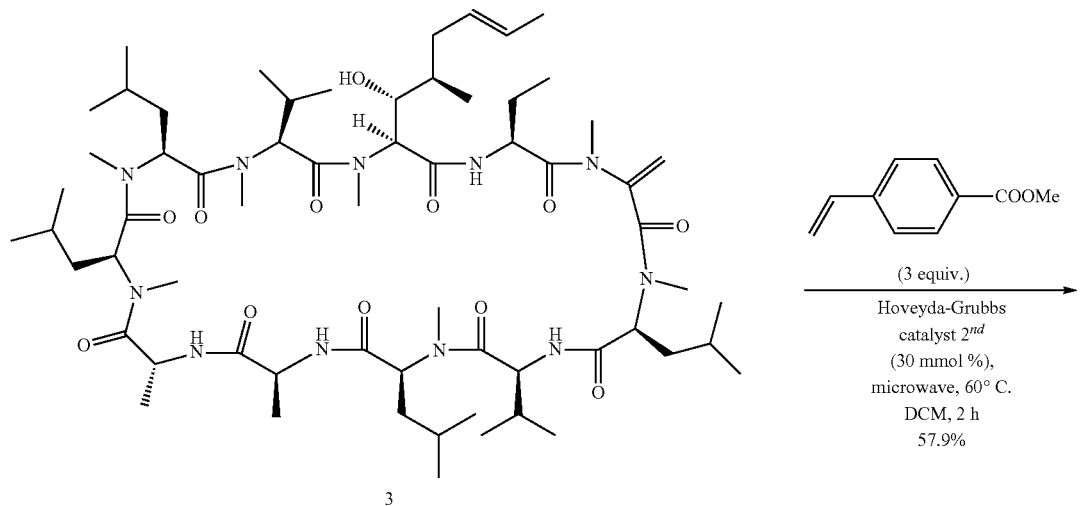

3

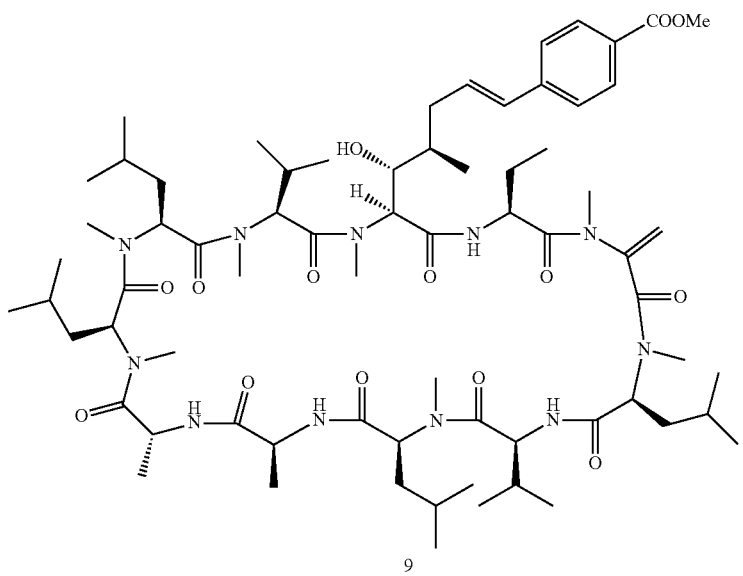

9

The compound 3 (40 mg, 0.033 mmol, 1 equiv.) was added to the special reaction flask for Biotag® microwave reactor, and dichloromethane (6 mL) was added for dissolving, then in the air, the substrate methyl p-vinyl benzoate (16 mg, 0.099 mmol, 3 equiv.) and Hoveyda-Grubbs catalyst 2$^{nd}$ (6.2 mg, 0.0099 mmol, 30 mol %) were added, the reaction flask was sealed and placed in the Biotage® Initiator+ microwave reactor at 60° C. to react for 1.5 hours. After the completion of the reaction, the reaction system was cooled to room temperature, and the organic solvent was removed by concentration under reduced pressure, then the remaining crude product was separated and purified by silica gel column chromatography (methyl tert-butyl ether:methanol=20:1), and the obtained mixture was further purified by semi-preparative HPLC. Then, 25.5 mg of white solid 9 was obtained with a yield of 57.9%.

Compound 9: $R_f$=0.30 (silica gel, TBME/MeOH=30:1, PMA);

$^1$H NMR (500 MHz, CDCl$_3$) δ 7.94 (d, J=8.3 Hz, 2H), 7.91 (d, J=9.4 Hz, 1H), 7.58 (dd, J=12.0, 8.1 Hz, 2H), 7.35 (d, J=8.1 Hz, 2H), 7.10 (d, J=7.9 Hz, 1H), 3.89 (s, 3H), 3.50 (s, 3H), 3.47 (s, 3H), 3.21 (s, 3H), 3.11 (s, 3H), 3.07 (s, 3H), 2.68 (s, 3H), 2.68 (s, 3H).

HRMS (ESI) m/z calcd for $C_{70}H_{115}N_{11}NaO_{14}^+$ ([M+Na]$^+$): 1356.8517; found: 1356.85168.

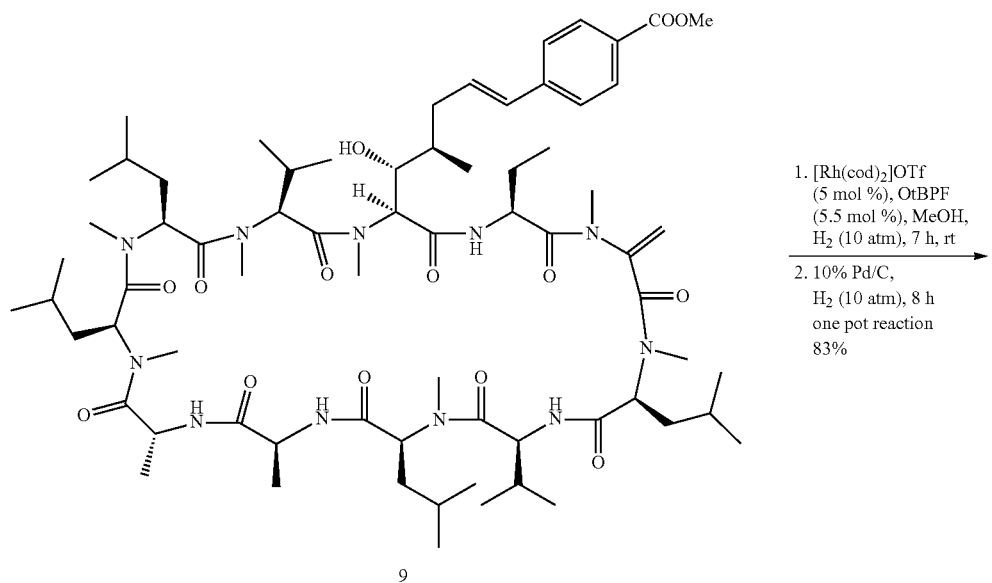

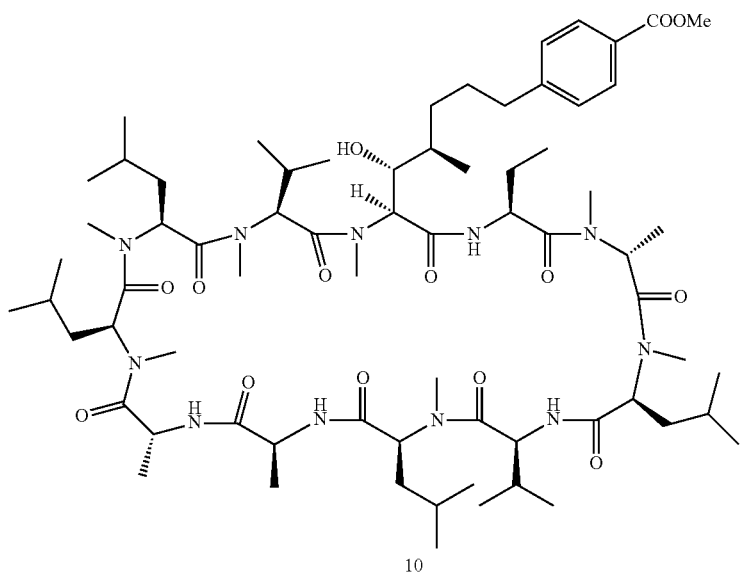

In a glove box filled with argon, [Rh(cod)₂]OTf (3.8 mg, 0.008 mmol) and DtBPF (4.2 mg, 0.0088 mmol) were weighed with a molar ratio of 1:1.1, and dissolved in dry methanol (1 mL)), then stirred at room temperature for about 1.0 minutes. A catalyst (140 µL, 5 mol %) was taken by a microsyringe into a hydrogenated flask containing the substrate 9 (30 mg, 0.0225 mmol, equiv.), and dry methanol (1.5 mL) solvent was added. The hydrogenation flask was carefully taken into the autoclave, then the gas in the autoclave was replaced with hydrogen for three times, and then 10 atm of hydrogen was slowly charged, then the reaction was stirred at room temperature for 7 hours, the hydrogen in the autoclave was slowly and carefully released in a fume cupboard, then the reaction still was opened, and the reaction solution was taken out, then filtered with diatomite, and then directly carded to the next step without purification.

The above reaction system was protected by argon, 10% Pd/C (20 mg) was added at 0° C., and the reaction system was replaced with a hydrogen balloon for 3 times, then the reaction was stirred overnight at room temperature. The reaction was detected by LCMS. After the reaction was completed, the reaction system was concentrated under vacuum and reduced pressure, and the crude product was filtered through diatomite to obtain 24.9 mg of pale yellow solid 10 with a yield of 83%.

Compound 10: $R_f$=0.35 (silica gel, TBME/MeOH=30:1, PMA);

$^1$H NMR (500 MHz, CDCl₃) δ 7.94-3.08 (s, 6H), 2.70 (s, 3H), 2.66 (s, 3H).

HRMS (ESI) m/z calcd for $C_{70}H_{119}N_{11}NaO_{14}^+$ ([M+Na]⁺): 1360.8830; found: 1360.88367.

Example 7

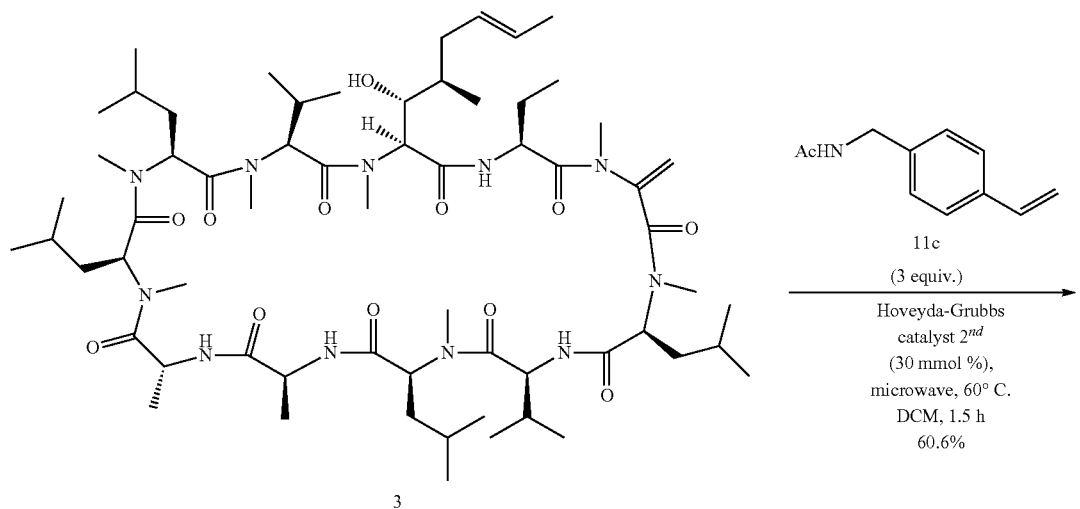

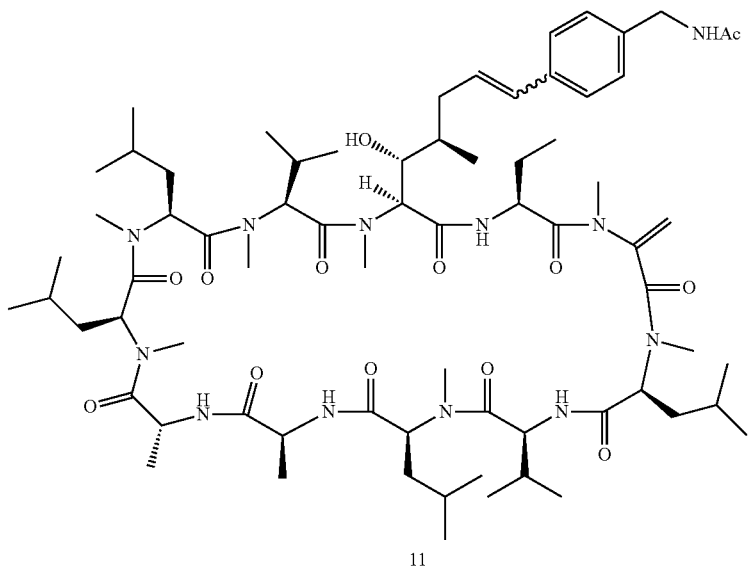

The synthesis of compound 11 refers to the method of synthesizing the compound 4. The compound 11 as a white solid (26.6 mg, 60.6% yield, E/Z: 94.2:5.8).

$R_f$=0.30 (silica gel, TBME/MeOH=30:1, PMA);

The $^1$H NMR of E-configuration of 11: $^1$H NMR (500 MHz, CDCl$_3$) δ 7.84 (d, J=9.5 Hz, 1H), 7.56 (d, J=8.8 Hz, 1H), 7.53 (d, J=7.4 Hz, 1H), 7.25 (s, 2H), 7.18 (d, J=7.8 Hz, 2H), 7.11 (d, J=7.9 Hz, 1H), 3.49 (s, 3H), 3.47 (s, 3H), 3.21 (s, 3H), 3.10 (s, 3H), 3.06 (s, 3H), 2.68 (s, 6H).

The $^1$H NMR of Z-configuration of 11: $^1$H NMR (500 MHz, CDCl$_3$) δ 7.69 (d, J=9.7 Hz, 1H), 7.54 (d, J=8.7 Hz, 1H), 7.48 (d, J=7.5 Hz, 1H), 7.15 (d, J=7.9 Hz, 1H), 3.50 (s, 3H), 3.48 (s, 3H), 3.20 (s, 3H), 3.10 (s, 3H), 3.05 (s, 3H), 2.59 (s, 3H), 2.58 (s, 3H).

HRMS (ESI) m/z calcd for $C_{71}H_{118}N_{12}NaO_{13}^+$ ([M+Na]$^+$): 1369.8834. found: 1369.88440.

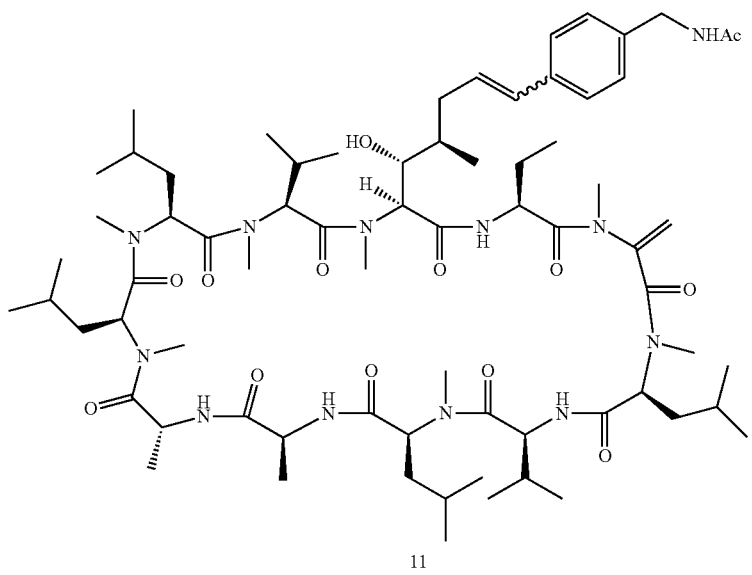
11
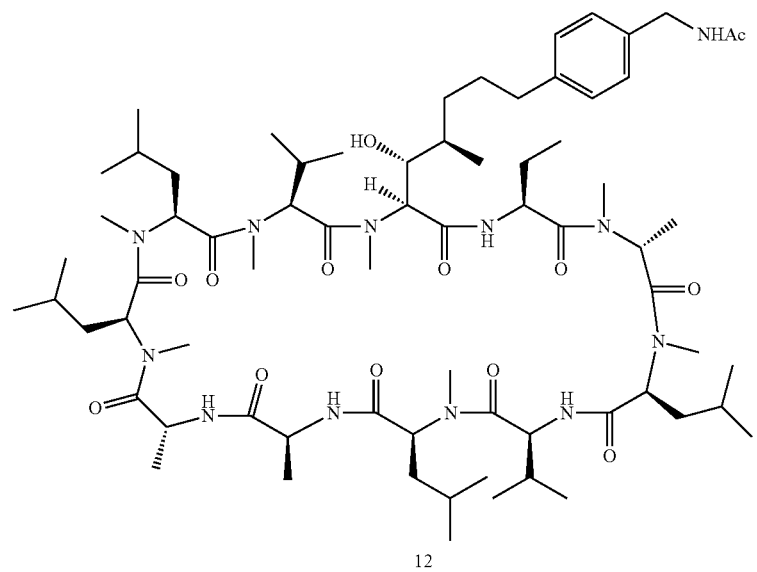
12
The synthesis of compound 12 refers to the method of synthesizing the compound 6. The compound 11 as a pale yellow solid (33 mg, 87% yield), $R_f$=0.35 (silica gel, TBME/MeOH=30:1, PMA);
$^1$H NMR (500 MHz, CDCl$_3$) δ 7.87 (d, J=9.9 Hz, 1H), 7.64 (d, J=7.7 Hz, 1H), 7.47 (d, J=8.1 Hz, 1H), 7.16 (d, J=7.9 Hz, 2H), 7.11 (dd, J=8.2, 2.4 Hz, 3H), 3.48 (s, 3H), 3.26 (s, 3H), 3.22 (s, 3H), 3.07 (s, 3H), 3.07 (s, 3H), 2.70 (s, 31.1), 2.67 (s, 3H).
HRMS (ESI): m/z: calcd for $C_{71}N_{122}N_{12}NaO_{13}^+$ ([M+Na]$^+$): 173.9147; found: 1373.91553.

Example 8

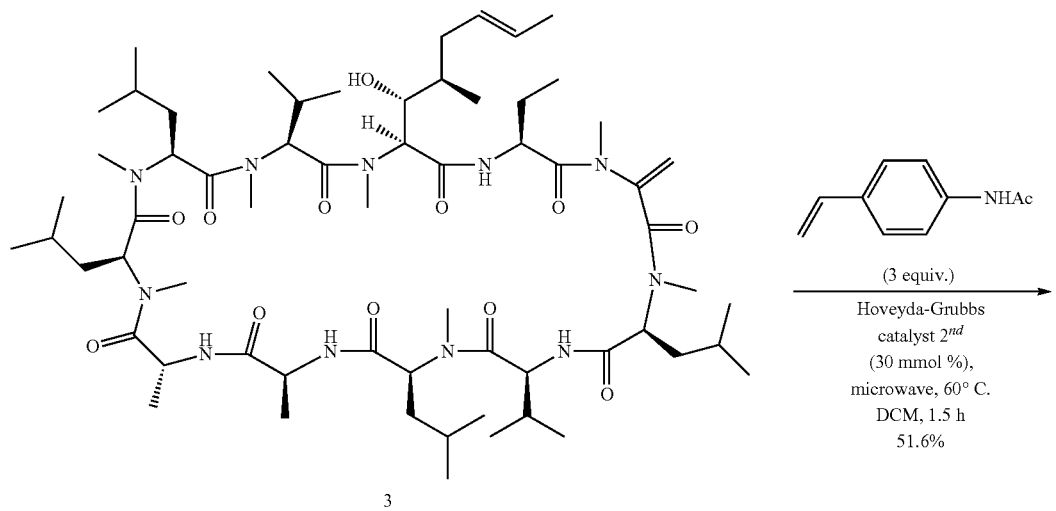

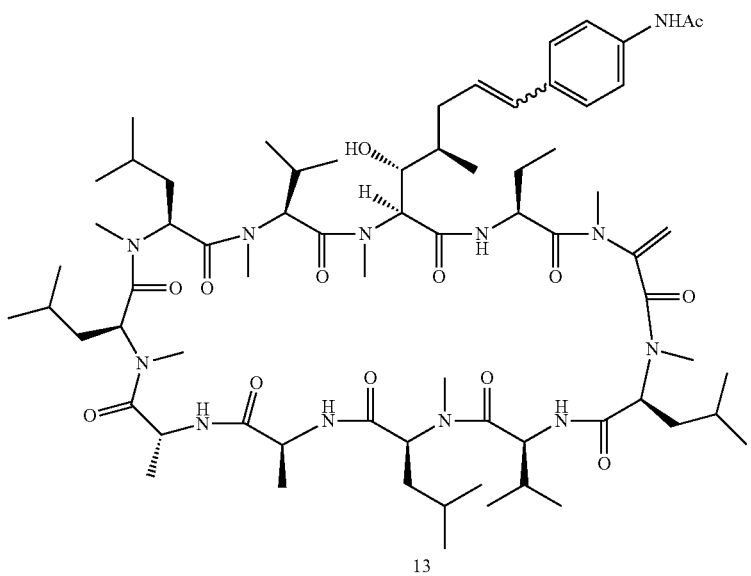

The synthesis of compound 13 refers to the method of synthesizing the compound 4. The compound 13 as a white solid (22.7 mg, 51.6% yield, E/Z: 16.2:1): $R_f$=0.30 (silica gel, TBME/MeOH=30:1, PMA); The $^1$H NMR of E-configuration of 13 $^1$H NMR (500 MHz, CDCl$_3$) δ 7.80 (d, J=9.5 Hz, 1H), 7.57 (d, J=8.7 Hz, 1H), 7.50 (d, J=7.3 Hz, 1H), 7.42 (d, J=8.3 Hz, 2H), 7.29 (s, 1H), 7.23 (d, J=8.4 Hz, 2H), 7.10 (d, J=7.9 Hz, 1H), 3.49 (s, 3H), 3.46 (s, 3H), 3.19 (s, 3H), 3.09 (s, 3H), 3.07 (s, 3H), 2.68 (s, 6H). The $^1$H NMR of Z-configuration of 13: $^1$H NMR (500 MHz, CDCl$_3$) δ 7.4 (d, J=9.6 Hz, 1H), 7.56 (d, J=8.6 Hz, 1H), 7.45 (d, J=7.2 Hz, 1H), 7.41 (d, J=8.2 Hz, 2H), 7.18 (d, J=8.3 Hz, 2H), 7.15 (d, J=7.9 Hz, 1H), 3.50 (s, 3H), 3.48 (s, 3H), 3.20 (s, 3H), 3.20 (s, 3H), 3.09 (s, 3H), 3.06 (s, 3H), 2.69 (s, 3H), 2.68 (s, 3H). HRMS (ESI) m/z calcd for $C_{70}H_{116}N_{12}NaO_{13}^+$ ([M+Na]$^+$): 1355.8677; found: 1355.86816.

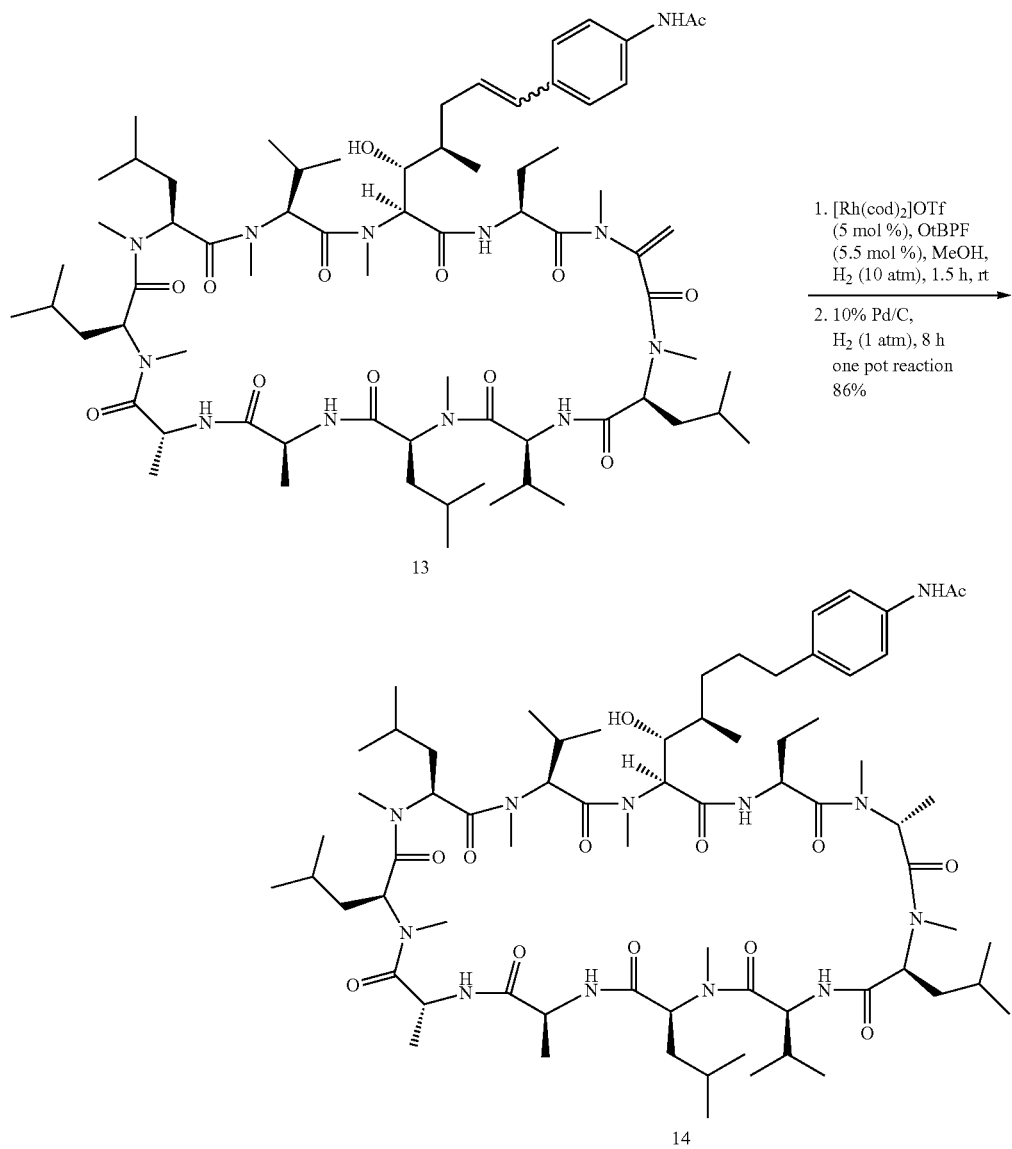

In a glove box filled with argon, [Rh(cod)₂]OTf (3.8 mg, 0.008 mmol) and DtBPF (4.2 mg, 0.0088 mmol) were weighed with a molar ratio of 1:1.1, and dissolved in dry methanol (1 mL)), then stirred at room temperature for about 10 minutes. A catalyst (93.7 μL, 5 mol %) was taken by a microsyringe into a reaction flask containing the substrate 13 (40 mg, 0.032 mmol, 1 equiv.), and dry methanol (1 mL) solvent was added. After replacing the gas in the reaction flask with a hydrogen balloon for three times, the reaction was stirred at room temperature and detected by LC/MS. After the completion of the reaction of double bond on P3 position, the reaction system was protected by argon, 10% Pd/C (30 mg) was added at 0° C., and the reaction system was replaced with a hydrogen balloon for 3 times, then the reaction was stirred overnight at room temperature. The reaction was detected by LCMS. After the reaction was completed, the reaction system was concentrated under vacuum and reduced pressure, and the crude product was filtered through diatomite to obtain 17 mg of pale yellow solid 14 with a yield of 86%.

Compound 14: $R_f$=0.35 (silica gel, TBME/MeOH=30:1, PMA);

$^1$H NMR (500 MHz, CDCl₃) δ 7.90 (d, J=9.9 Hz, 1H), 7.65 (d, J=7.7 Hz, 1H), 7.49 (d, J=8.1 Hz, 1H), 7.37 (d, J=8.1 Hz, 2H), 7.27 (s, 1H), 7.13-7.08 (m, 4H), 3.48 (s, 3H), 3.27 (s, 3H), 3.23 (s, 3H), 3.08 (s, 6H), 2.71 (s, 3H), 2.67 (s, 3H).

HRMS (ESI) m/z calcd for $C_{70}H_{120}N_{12}NaO_{13}^+$ ([M+Na]⁺): 1359.8990, found: 1359.89990.

Each of the technical features of the above-mentioned embodiments may be combined arbitrarily in any suitable way. To simplify the description, not all the possible combinations of each of the technical features in the above embodiments are described. However, all of the combinations of these technical features should be considered as within the scope of this disclosure, as long as such combinations do not contradict with each other.

The above-mentioned embodiments only describe several embodiments of the present disclosure, which facilitate a specific and detailed understanding of the technical solutions of the present disclosure, but they cannot be understood to limit the protection scope of the present disclosure. It should be noted that a plurality of variations and modifications may be made by those skilled in the art without departing from the scope of the present disclosure, which are all within the scope of protection of the present disclosure. It should be understood that technical solutions obtained by those skilled in the art through logical analysis, reasoning or limited experiments on the basis of the technical solutions provided by the present disclosure are all within the protection scope of the appended claims of the present disclosure.

What is claimed is:

1. A method of synthesizing a cyclosporine derivative represented by the following Formula (I):

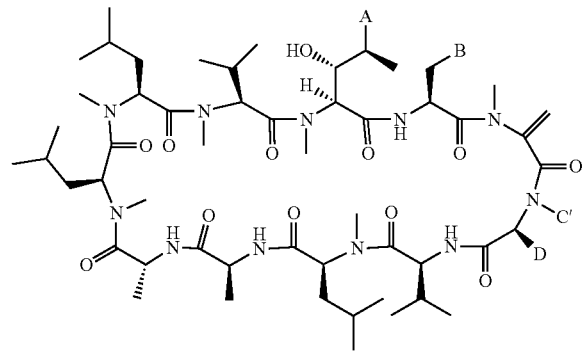

Formula (I)

wherein A is at least one selected from the group consisting of —CH$_2$—CH=CHR, —CH=CH—CH=CHR, and —CH$_2$CH$_2$R; R is at least one selected from the group consisting of —CH$_3$, —CH$_2$SH, —CH$_2$S—R$_1$, —CH$_2$—COOR$_1$', —COOR$_1$', —R$_2$—COOR$_1$', and CH$_2$—R$_2$—COOR$_1$'; R$_1$ is C1~C6 alkyl; R$_2$ is C1~C6 alkoxy; R$_1$' is H, ammonium salt or C1~C6 alkyl;

B is at least one selected from the group consisting of —CH$_3$, —CH$_2$CH$_3$, —CH(OH)CH$_3$, —CH(CH$_3$)$_2$, and —CH$_2$CH$_2$CH$_3$;

C' is at least one selected from the group consisting of —H, —CH$_3$, —CH$_2$CH$_3$, and —CH$_2$CH$_2$CH$_3$; and D is at least one selected from the group consisting of —CH$_2$CH(CH$_3$)$_2$, —CH$_2$C(OH)(CH$_3$)$_2$, —CH(CH$_3$)CH$_2$CH$_3$, and —CH$_2$CH$_2$[4-(2-CH$_3$OCH$_2$CH$_2$)-1-R$_3$];

R$_3$ is piperazinyl;

the method comprising:

providing a precursor fluid, an alkaline fluid, and a ClCH$_2$OCOCl solution; wherein a precursor in the precursor fluid is represented by Formula (II):

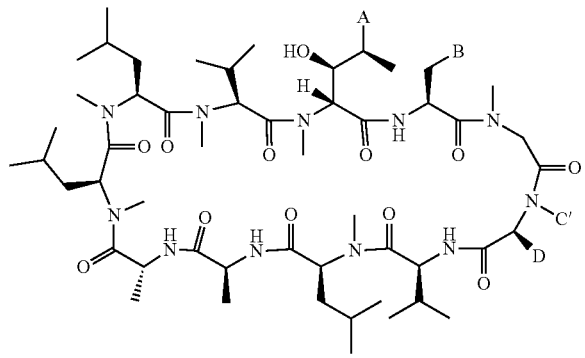

Formula (II)

premixing the precursor fluid and the alkaline fluid to obtain a premixed solution;

feeding the premixed solution into a first reaction chamber, reacting to prepare a first reaction liquid;

feeding the first reaction liquid into a second reaction chamber, reacting the first reaction liquid with a CO$_2$ fluid to prepare a second reaction liquid; and reacting the second reaction liquid with the ClCH$_2$OCOCl solution.

2. The method according to claim 1, wherein the precursor fluid is fed with a flow rate of 0.03 mM/min to 0.06 mM/min; and the alkaline fluid is fed with a flow rate of 0.1 mM/min to 0.5 mM/min.

3. The method according to claim 1, wherein the precursor fluid and the alkaline fluid are fed into the first reaction chamber at a temperature of −5° C. to 30° C. and with a time of 50 s to 90 s.

4. The method according to claim 1, wherein the CO$_2$ fluid has a flow rate of 5 mL/min to 12 mL/min.

5. The method according to claim 1, wherein the first reaction liquid is fed into the second reaction chamber to react with the CO$_2$ fluid at a temperature of −20° C. to 30° C. and with a time of 3 s to 20 s.

6. The method according to claim 1, wherein a molar concentration of ClCH$_2$OCOCl solution is 0.3 M to 0.7 M.

7. The method according to claim 1, wherein the molar concentration of the precursor in the precursor fluid is 0.01 M to 0.055 M.

8. The method according to claim 1, wherein the molar concentration of alkali in the alkaline fluid is 0.1 M to 0.3 M.

9. The method according to claim 1, wherein the molar ratio of the precursor, alkali and CO$_2$ is 1:(8~15):(8~25).

10. The method according to claim 1, wherein reacting the second reaction liquid with the ClCH$_2$OCOCl solution comprises:

collecting the second reaction liquid into the ClCH$_2$OCOCl solution at a temperature of −55° C. to −45° C. to prepare a third reaction solution; and warming the third reaction solution to room temperature naturally and reacting for 3 h to 20 h.

11. The method according to claim 1, wherein solvents of the precursor fluid, the alkaline fluid and the ClCH$_2$OCOCl solution are at least one selected from the group consisting of 2-methyltetrahydrofuran, tetrahydrofuran, n-hexane, methyl tert-butyl ether, and diethyl ether.

12. The method according to claim 10, further comprising:

adding water to the third reaction solution to adjust the pH of the third reaction solution to 7 to 8;

concentrating the third reaction solution under reduced pressure;
extracting the third reaction solution with ethyl acetate, and collecting an organic phase; and
purifying the organic phase by column chromatography.

13. The method according to claim 12, wherein a mobile phase used in the column chromatography is dichloromethane and methanol with a volume ratio of (15~25):1.

14. The method according to claim 1, wherein the precursor is cyclosporine A; A is —CH$_2$—CH=CH—CH$_3$; B is —CH$_3$; C' is —CH$_3$; and D is —CH$_2$CH(CH$_3$)$_2$.

15. The method according to claim 1, wherein an alkali in the alkaline fluid is at least one selected from the group consisting of lithium diisopropylamide, lithium bis(trimethylsilyl)amide, and sodium bis(trimethylsilyl)amide.

16. A method of synthesizing a cyclosporine 1,3-position derivative, comprising:
synthesizing a cyclosporine derivative H according to the method of claim 1;
performing an olefin metathesis action using the cyclosporine derivative H and a compound CH$_2$=CH—R to prepare an intermediate H-1;
performing an asymmetric hydrogenation reaction to the intermediate H-1 to prepare an intermediate H-2; and
performing a hydrogenation reaction to the intermediate H-2 to prepare the cyclosporine 1,3-position derivative;
wherein the cyclosporine derivative H is represented by the following Formula (III):

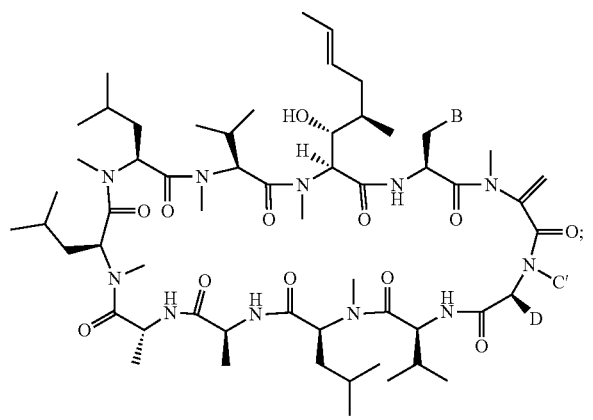

Formula (III)

the intermediate H-1 is represented by the following Formula (III-1):

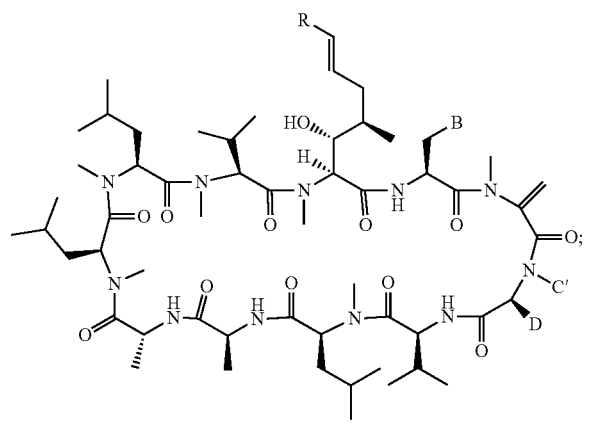

Formula (III-1)

the intermediate H-2 is represented by the following Formula (III-2):

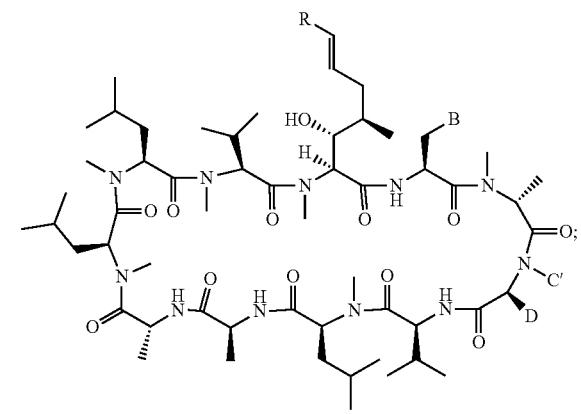

Formula (III-2)

and the cyclosporine 1,3-position derivative is represented by the following Formula (IV):

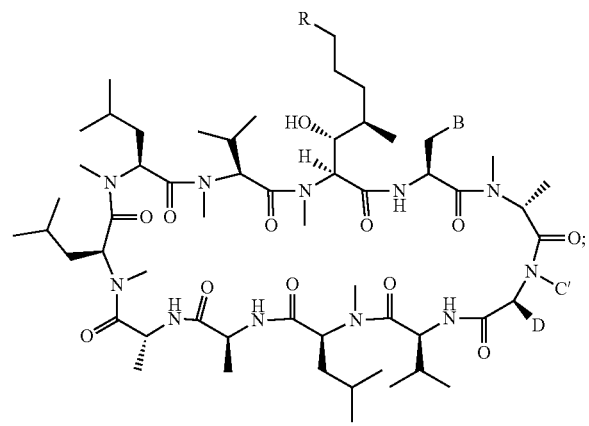

Formula (IV)

wherein R is at least one selected from the group consisting of —CH$_2$CH$_2$CH$_2$NH(C=O)CH$_3$, —CH$_2$CH$_2$CH$_2$COOH, and the following groups:

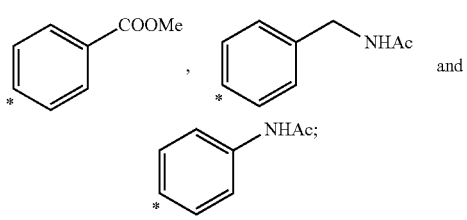

wherein the asterisk indicates the point of attachment.

17. The method according to claim 16, wherein the olefin metathesis action comprises a reflux reaction using dichloromethane as a solvent.